(12) United States Patent
Kim et al.

(10) Patent No.: US 9,574,104 B1
(45) Date of Patent: Feb. 21, 2017

(54) COMPOSITIONS AND PROCESSES FOR SELF-ASSEMBLY OF BLOCK COPOLYMERS

(71) Applicant: AZ ELECTRONIC MATERIALS (LUXEMBOURG) S.A.R.L., Luxembourg (LU)

(72) Inventors: JiHoon Kim, North Wales, PA (US); Jian Yin, Bridgewater, NJ (US); Hengpeng Wu, Hillsborough, NJ (US); Jianhui Shan, Branchburg, NJ (US); Guanyang Lin, Whitehouse Station, NJ (US)

(73) Assignee: AZ ELECTRONIC MATERIALS (LUXEMBOURG) S.A.R.L., Luxembourg (LU)

( * ) Notice: Subject to any disclaimer, the term of this patent is extended or adjusted under 35 U.S.C. 154(b) by 0 days.

(21) Appl. No.: 14/885,328

(22) Filed: Oct. 16, 2015

(51) Int. Cl.
  *C09D 133/12* (2006.01)
  *G03F 7/00* (2006.01)
  (Continued)

(52) U.S. Cl.
  CPC ........... *C09D 133/12* (2013.01); *C08F 220/18* (2013.01); *C08L 53/00* (2013.01); *G03F 7/0002* (2013.01);
  (Continued)

(58) Field of Classification Search
  CPC ........... G03F 7/0002; G03F 7/30; G03F 7/40; H01L 21/0274; H01L 21/0276; H01L 21/0275; C08F 293/00; C08L 53/00; C08L 33/12
  (Continued)

(56) References Cited

U.S. PATENT DOCUMENTS 7,521,094 B1   4/2009   Cheng et al.
7,560,141 B1   7/2009   Kim et al.
(Continued)

OTHER PUBLICATIONS

Eungnak Han et al., "Photopatternable Imaging Layers for Controlling Block Copolymer Microdomain Orientation", Advanced Materials vol. 19, pp. 4448-4452 (2007).
(Continued)

*Primary Examiner* — Amanda C Walke
(74) *Attorney, Agent, or Firm* — Mitchell Brustein

(57) ABSTRACT

The present invention relates to novel copolymers containing cross-linkable and graft-able moieties, novel compositions comprised of these novel copolymers and a solvent, and methods for using these novel compositions to form neutral layer films which are both cross-linked and grafted on the substrate which are used in processes for aligning microdomains of block copolymers (BCP) on this neutral layer coated substrate such as self-assembly and directed self-assembly. The novel compositions are comprised of at least one novel random copolymer comprised of least one unit of structure (1), at least one unit of structure (2) at least one unit of structure (3) one ∼∼ H end group and one end group having structure (1');

(Continued)

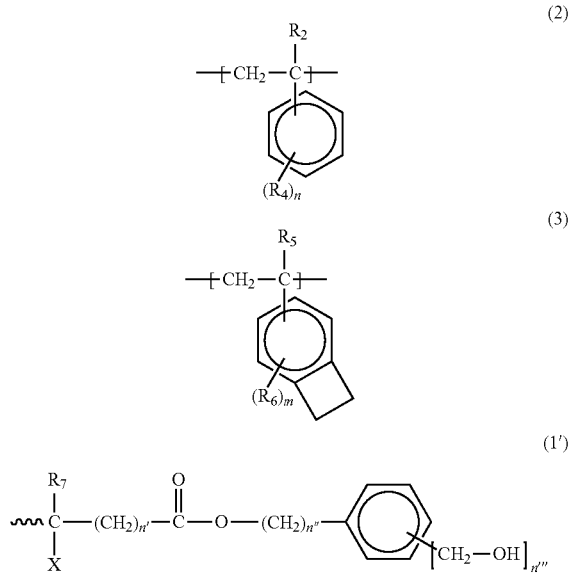

where $R_1$ is selected from the group consisting of a $C_1$-$C_8$ alkyl, $C_1$-$C_8$ fluoroalkyl, $C_1$-$C_8$ partially fluorinated alkyl moiety, $C_4$-$C_8$ cycloalkyl, $C_4$-$C_8$ cyclofluoroalkyl, $C_4$-$C_8$ partially fluorinated cycloalkyl, and a $C_2$-$C_8$ hydroxyalkyl; $R_2$, $R_3$ and $R_5$ are independently selected from a group consisting of H, $C_1$-$C_4$ alkyl, $CF_3$ and F; $R_4$ is selected from the group consisting of H, $C_1$-$C_8$ alkyl, $C_1$-$C_8$ partially fluorinated alkyl moiety and $C_1$-$C_8$ fluoroalkyl, n ranges from 1 to 5, $R_6$ is selected from the group consisting of H, F, $C_1$-$C_8$ alkyl and a $C_1$-$C_8$ fluoroalkyl and m ranges from 1 to 3, and n' ranges from 1 to 5, and n" ranges from 1 to 5, n''' ranges from 1 to 5, $R_7$ is a $C_1$ to $C_8$ alkyl and X is —CN, or an alkyloxycarbonyl moiety $R_8$—O—(C=O)— where $R_8$ is a $C_1$ to $C_8$ alkyl and ∿∿ represent the attachment point of the end group to the polymer. The novel polymers, compositions and processes are useful for fabrication of electronic devices.

16 Claims, 6 Drawing Sheets

(51) Int. Cl.

| | | |
|---|---|---|
| *C08F 220/18* | (2006.01) | |
| *G03F 7/11* | (2006.01) | |
| *G03F 7/16* | (2006.01) | |
| *G03F 7/20* | (2006.01) | |
| *H01L 21/027* | (2006.01) | |
| *C08L 53/00* | (2006.01) | |
| *G03F 7/40* | (2006.01) | |

(52) U.S. Cl.
CPC ............... *G03F 7/11* (2013.01); *G03F 7/168* (2013.01); *G03F 7/20* (2013.01); *G03F 7/40* (2013.01); *H01L 21/0273* (2013.01); *H01L 21/0274* (2013.01); *H01L 21/0276* (2013.01)

(58) Field of Classification Search
USPC . 430/322, 323, 325, 329, 330, 331; 526/319
See application file for complete search history.

(56) References Cited

U.S. PATENT DOCUMENTS

| | | | | |
|---|---|---|---|---|
| 8,691,925 | B2* | 4/2014 | Wu | C08F 293/00 |
| | | | | 430/296 |
| 8,835,581 | B2 | 9/2014 | Wu et al. | |
| 9,109,086 | B2* | 8/2015 | Tang | C08F 290/02 |
| 2004/0068071 | A1* | 4/2004 | Hoff | B32B 27/08 |
| | | | | 526/319 |
| 2009/0286927 | A1* | 11/2009 | Sodergard | C08G 63/06 |
| | | | | 524/599 |
| 2014/0193754 | A1* | 7/2014 | Wu | C08F 293/00 |
| | | | | 430/296 |
| 2014/0299969 | A1* | 10/2014 | Xu | B81C 1/00031 |
| | | | | 257/618 |
| 2014/0342290 | A1 | 11/2014 | Wu et al. | |
| 2015/0197594 | A1* | 7/2015 | Xu | C09D 153/00 |
| | | | | 428/195.1 |

OTHER PUBLICATIONS

Craig J. Hawker et al., "Facile Synthesis of Block Copolymers for Nanolithographic Applications", Polymer Preprints vol. 46 No. 2, pp. 239-248 (2005).
Craig J. Hawker et al., "Initiating Systems for Nitroxide-Mediated "Living" Free Radical Polymerizations: Synthesis and Evaluation", Macromolecules vol. 29 No. 16, pp. 5245-5254 (1996).
E. Huang et al., "Using Surface Active Random Copolymers to Control the Domain Orientation in Diblock Copolymer Thin Films", Macromolecules vol. 31 No. 22, pp. 7641-7650 (1998).
Yoojin Kim et al., "The Dramatic Effect of Architecture on the Self-Assembly of Block Copolymers at Interfaces", Langmuir vol. 21 No. 23, pp. 10444-10458 (2005).
Julie M. Leiston-Belanter et al., "A Thermal and Manufacturable Approach to Stabilized Diblock Copolymer Templates" Macromolecules vol. 38 No. 18, pp. 7676-7683 (2005).
Du Yeol Ryu et al., "A Generalized Approach to the Modification of Solid Surfaces", Science vol. 308, pp. 236-239 (2005).
Du Yeol Ryu et al., "Surface Modification with Cross-Linked Random Copolymers: Minimum Effective Thickness", Macromolecules vol. 40 No. 12, pp. 4296-4300 (2007).

\* cited by examiner

Figure 1
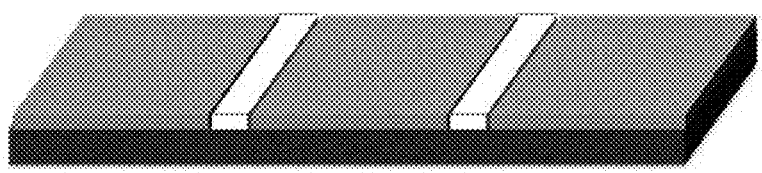
Figure 1 a
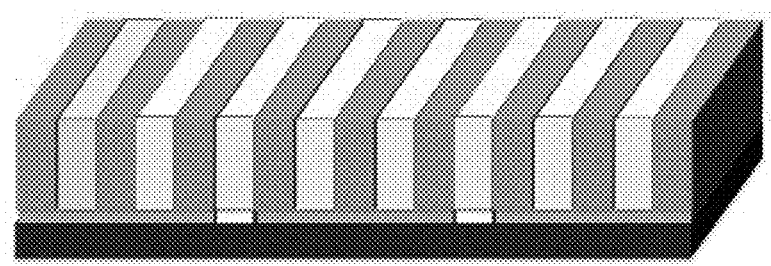
Figure 1 b
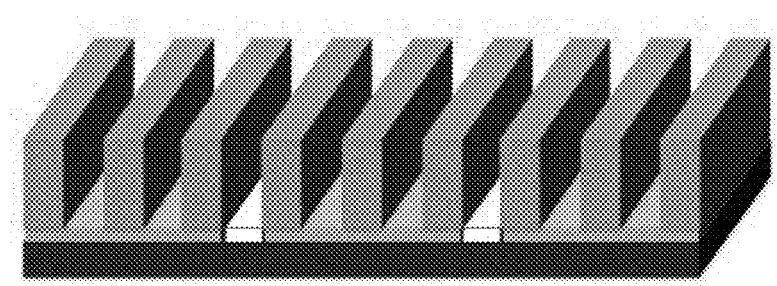
Figure 1 c

Figure 3
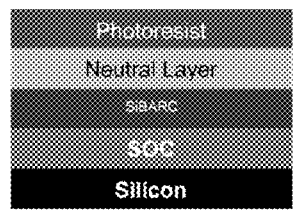
Figure 3a
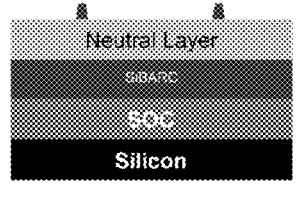
Figure 3b
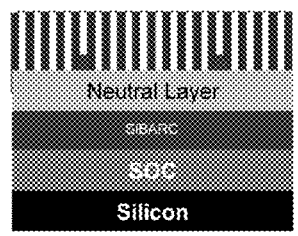
Figure 3c
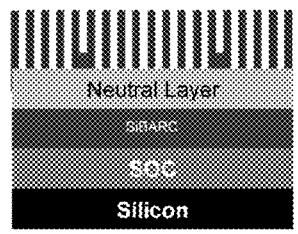
Figure 3d
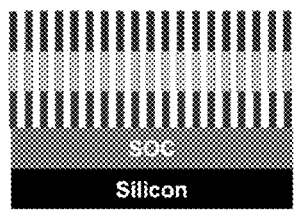
Figure 3e
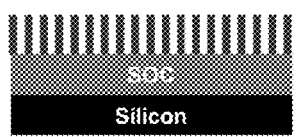
Figure 3f
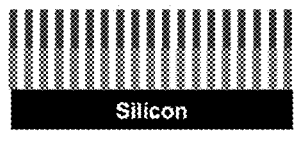
Figure 3g

Figure 4
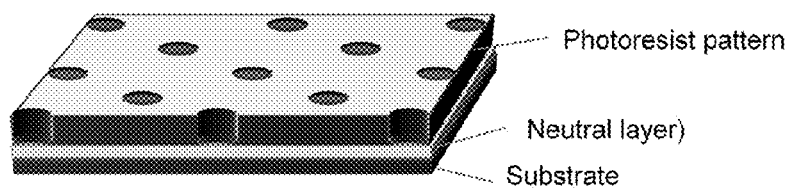
Figure 4a
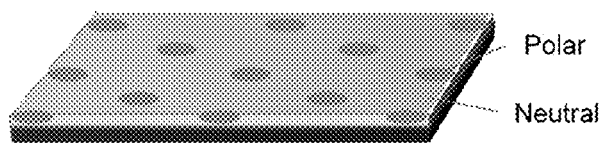
Figure 4b
Figure 4c
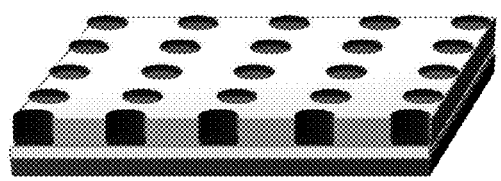
Figure 4d

COMPOSITIONS AND PROCESSES FOR SELF-ASSEMBLY OF BLOCK COPOLYMERS

FIELD OF THE INVENTION

The invention relates to novel polymers, novel compositions and novel methods for using the novel compositions for aligning microdomains of directed self-assembling block copolymers (BCP). The compositions and processes are useful for fabrication of electronic devices.

DESCRIPTION OF THE INVENTION

Directed self-assembly of block copolymers is a method useful for generating smaller and smaller patterned features for the manufacture of microelectronic devices in which the critical dimensions (CD) of features on the order of nanoscale can be achieved. Directed self-assembly methods are desirable for extending the resolution capabilities of microlithographic technology. In a conventional lithography approach, ultraviolet (UV) radiation may be used to expose through a mask onto a photoresist layer coated on a substrate or layered substrate. Positive or negative photoresists are useful and these can also contain a refractory element such as silicon to enable dry development with conventional integrated circuit (IC) plasma processing. In a positive photoresist, UV radiation transmitted through a mask causes a photochemical reaction in the photoresist such that the exposed regions are removed with a developer solution or by conventional IC plasma processing. Conversely, in negative photoresists, UV radiation transmitted through a mask causes the regions exposed to radiation to become less removable with a developer solution or by conventional IC plasma processing. An integrated circuit feature, such as a gate, via or interconnect, is then etched into the substrate or layered substrate, and the remaining photoresist is removed. When using conventional lithographic exposure processes, the dimensions of features of the integrated circuit feature are limited. Further reduction in pattern dimensions are difficult to achieve with radiation exposure due to limitations related to aberrations, focus, proximity effects, minimum achievable exposure wavelengths and maximum achievable numerical apertures. The need for large-scale integration has led to a continued shrinking of the circuit dimensions and features in the devices. In the past, the final resolution of the features has been dependent upon the wavelength of light used to expose the photoresist, which has its own limitations. Direct assembly techniques, such as graphoepitaxy and chemoepitaxy using block copolymer imaging, are highly desirable techniques used to enhance resolution while reducing CD variation. These techniques can be employed to either enhance conventional UV lithographic techniques or to enable even higher resolution and CD control in approaches employing EUV, e-beam, deep UV or immersion lithography. The directed self-assembly block copolymer comprises a block of etch resistant copolymeric unit and a block of highly etchable copolymeric unit, which when coated, aligned and etched on a substrate give regions of very high density patterns.

In the graphoepitaxy directed self-assembly method, the block copolymers self organizes around a substrate that is pre-patterned with conventional lithography (Ultraviolet, Deep UV, e-beam, Extreme UV (EUV) exposure source) to form repeating topographical features such as a line/space (L/S) or contact hole (CH) pattern. In an example of a US directed self-assembly array, the block copolymer can form self-aligned lamellar regions which can form parallel line-space patterns of different pitches in the trenches between pre-patterned lines, thus enhancing pattern resolution by subdividing the space in the trench between the topographical lines into finer patterns. For example, a diblock copolymer which is capable of microphase separation and comprises a block rich in carbon (such as styrene or containing some other element like Si, Ge, Ti) which is resistant to plasma etch, and a block which is highly plasma etchable or removable, can provide a high resolution pattern definition. Examples of highly etchable blocks can comprise monomers which are rich in oxygen and which do not contain refractory elements, and are capable of forming blocks which are highly etchable, such as methylmethacrylate. The plasma etch gases used in the etching process of defining the self-assembly pattern typically are those used in processes employed to make integrated circuits (IC). In this manner very fine patterns can be created in typical IC substrates than were definable by conventional lithographic techniques, thus achieving pattern multiplication. Similarly, features such as contact holes can be made denser by using graphoepitaxy in which a suitable block copolymer arranges itself by directed self-assembly around an array of contact holes or posts defined by conventional lithography, thus forming a denser array of regions of etchable and etch resistant domains which when etched give rise to a denser array of contact holes. Consequently, graphoepitaxy has the potential to offer both pattern rectification and pattern multiplication.

In chemical epitaxy or pinning chemical epitaxy the self-assembly of the block copolymer is formed around a surface that has regions of differing chemical affinity but no or very slight topography to guide the self-assembly process. For example, the surface of a substrate could be patterned with conventional lithography (UV, Deep UV, e-beam EUV) to create surfaces of different chemical affinity in a line and space (L/S) pattern in which exposed areas whose surface chemistry had been modified by irradiation alternate with areas which are unexposed and show no chemical change. These areas present no topographical difference, but do present a surface chemical difference or pinning to direct self-assembly of block copolymer segments. Specifically, the directed self-assembly of a block copolymer whose block segments contain etch resistant (such as styrene repeat unit) and rapidly etching repeat units (such as methyl methacrylate repeat units) would allow precise placement of etch resistant block segments and highly etchable block segments over the pattern. This technique allows for the precise placement of these block copolymers and the subsequent pattern transfer of the pattern into a substrate after plasma or wet etch processing. Chemical epitaxy has the advantage that it can be fined tuned by changes in the chemical differences to help improve line-edge roughness and CD control, thus allowing for pattern rectification. Other types of patterns such as repeating contact holes (CH) arrays could also be pattern rectified using chemoepitaxy.

Neutral layers are layers on a substrate, or the surface of a treated substrate, which have no affinity for either of the block segment of a block copolymer employed in directed self-assembly. In the graphoepitaxy method of directed self-assembly of block copolymer, neutral layers are useful as they allow the proper placement or orientation of block polymer segments for directed self-assembly which leads to proper placement of etch resistant block polymer segments and highly etchable block polymer segments relative to the substrate. For instance, in surfaces containing line and space features which have been defined by conventional radiation lithography, a neutral layer allows block segments to be oriented so that the block segments are oriented perpendicular to the surface of the substrates, an orientation which is ideal for both pattern rectification and pattern multiplication depending on the length of the block segments in the block copolymer as related to the length between the lines defined by conventional lithography. If a substrate interacts too strongly with one of the block segments it would cause it to lie flat on that surface to maximize the surface of contact between the segment and the substrate; such a surface would perturb the desirable perpendicular alignment which can be used to either achieve pattern rectification or pattern multiplication based on features created through conventional lithography. Modification of selected small areas or pinning of substrate to make them strongly interactive with one block of the block copolymer and leaving the remainder of the surface coated with the neutral layer can be useful for forcing the alignment of the domains of the block copolymer in a desired direction, and this is the basis for the pinned chemoepitaxy or graphoepitaxy employed for pattern multiplication.

There is a need for novel copolymers which can be coated from a novel formulation comprised of these novel copolymers and a solvent, and which after coating can form a cross-linked grafted neutral polymer layer on semiconductor (e.g. Si, GaAs, and the like), metal (Cu, W, Mo, Al, Zr, Ti, Hf, Au and the like) and metal oxide (Copper oxide, Aluminum oxide, Hafnium oxide, Zirconium oxide, Titanium oxide and the like) substrates through a simple spin coating, followed by a post coat bake to affect both chemical bonding to the substrate by grafting and crosslinking of the layer. There is also a need for novel polymer which can be used in novel compositions which when formed into a layer remain neutral to the self-assembly block copolymer and yet are not damaged by processing steps of directed self-assembly techniques, and can further enhance the lithographic performance of the directed self-assembly materials and processes, especially reducing the number of processing steps and providing better pattern resolution with good lithographic performance and do not undergo any defect formation caused by de-wetting of the neutral layer from the substrate on which it is applied. The present invention relates to novel processes, novel copolymers, and novel compositions which form cross-linked and grafted layers which are neutral to the self-assembly block copolymer and provide patterns with good lithographic performance. Furthermore, the combination of both grafting and crosslinking functionality in the neutral layer polymer unexpectedly avoids problems with de-wetting of the neutral layer which were unexpectedly found when the neutral layer copolymer only incorporated crosslinking functionality.

DETAILED DESCRIPTION OF DRAWINGS

FIGS. 1a to 1c show a self-alignment process.

FIGS. 3a to 3g show a process for positive tone multiplication.

FIGS. 4a to 4d show a contact hole process.

Figure 5:
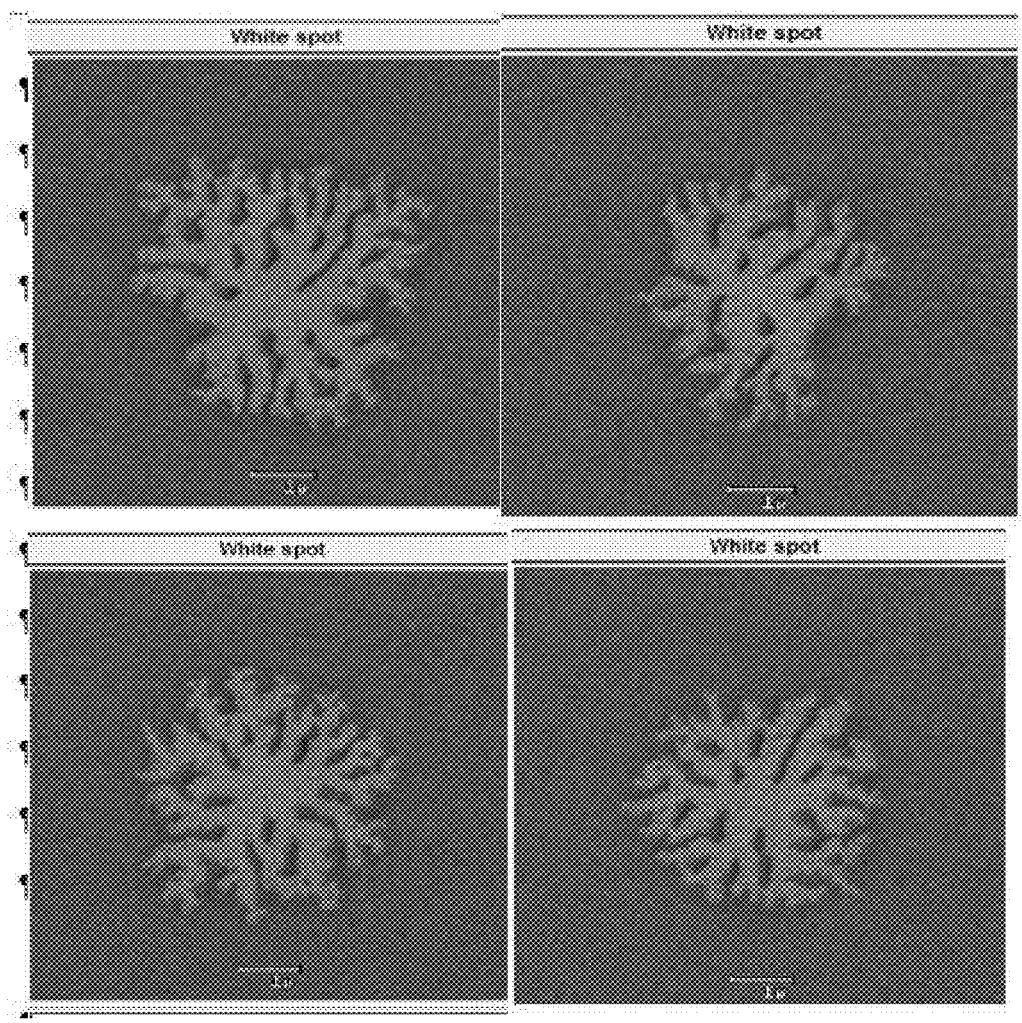

FIG. 5. shows SEM images of de-wetting defects of film spun from a formulation made of copolymer from Synthesis Example 1.

Figure 6:
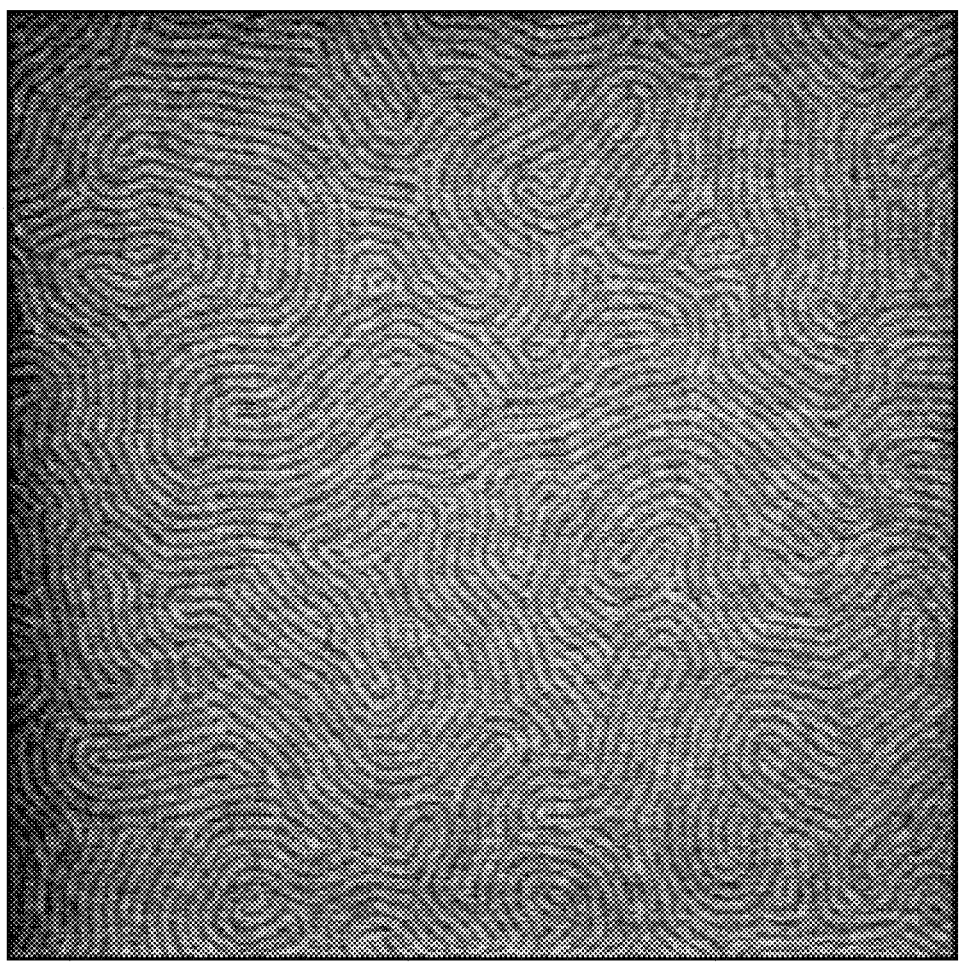

FIG. 6. shows self-assembly of a block copolymer on a film spun from a formulation made of the copolymer from Synthesis Example 2b.

SUMMARY OF INVENTION

A novel composition comprising at least one novel random copolymer having at least one unit of structure (1), at least one unit of structure (2) at least one unit of structure (3) one 〰 H end group and one end group having structure (1');

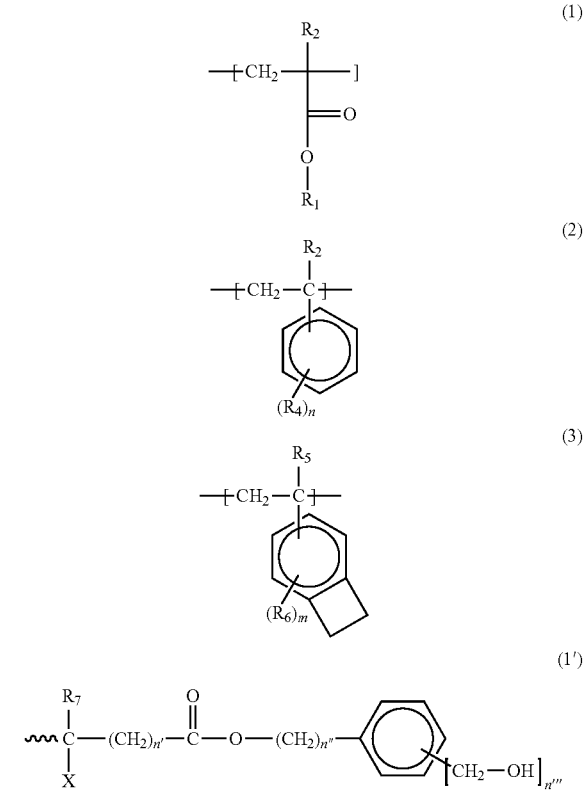

where $R_1$ is selected from the group consisting of a $C_1$-$C_8$ alkyl, $C_1$-$C_8$ fluoroalkyl, $C_1$-$C_8$ partially fluorinated alkyl moiety, $C_4$-$C_8$ cycloalkyl, $C_4$-$C_8$ cyclofluoroalkyl, $C_4$-$C_8$ partially fluorinated cycloalkyl, and a $C_2$-$C_8$ hydroxyalkyl; $R_2$, $R_3$ and $R_5$ are independently selected from a group consisting of H, $C_1$-$C_4$ alkyl, $CF_3$ and F; $R_4$ is selected from the group consisting of H, $C_1$-$C_8$ alkyl, $C_1$-$C_8$ partially fluorinated alkyl moiety and $C_1$-$C_8$ fluoroalkyl, n ranges from 1 to 5, $R_6$ is selected from the group consisting of H, F, $C_1$-$C_8$ alkyl and a $C_1$-$C_8$ fluoroalkyl and m ranges from 1 to 3, and n' ranges from 1 to 5, and n" ranges from 1 to 5, n''' ranges from 1 to 5, $R_7$ is a $C_1$ to $C_8$ alkyl and X is —CN, or an alkyloxycarbonyl moiety $R_8$—O—(C=O)— where $R_8$ is a $C_1$ to $C_8$ alkyl and 〰 represent the attachment point of the end group to the copolymer.

The present invention also relates to novel processes for forming patterns using self-assembly or directed self-aligned lithography using these novel composition.

DETAILED DESCRIPTION OF THE INVENTION

Herein, alkyl refers to saturated hydrocarbon groups which can be linear or branched (e.g. methyl, ethyl, propyl, isopropyl, tert-butyl and the like), cycloalkyl refers to a hydrocarbon containing one saturated cycle (e.g. cyclohexyl, cyclopropyl, cyclopentyl and the like), fluoroalkyl refers to a linear or branched saturated alkyl group in which all the hydrogens have been replaced by fluorine, cyclofluoroalkyl refers to a cycloalkyl group in which all the hydrogens have been replaced by fluorine, partially fluorinated alkyl refers to a linear or branched saturated alkyl group in which part of the hydrogens have been replaced by fluorine, partially fluorinated cycloalkyl refers to a cycloalkyl group in which part of the hydrogens have been replaced by fluorine, hydroxyalkyl refers to an alkyl or cycloalkyl group which is substituted with a least one hydroxyl moiety (e.g. —CH$_2$—CH$_2$—OH, CH—CH(OH)—CH$_3$ and the like).

The present invention relates to novel copolymers, compositions, and novel self-assembly and directed self-assembly processes for forming patterns with high resolution and good lithographic properties. The novel composition comprised of the novel copolymer and a solvent is capable of forming a neutral layer for use with self-assembly and directed self-assembly of block copolymers. The neutral layer is an orientation control layer which allows the block copolymer coated above the neutral layer to align in the desirable direction relative to the substrate for obtaining high resolution lithography. The invention also relates to novel processes for use in directed self-assembly of block copolymers, such as graphoepitaxy and chemoepitaxy, which use the neutral layer compositions. The invention leads to further improvement in resolution or CD uniformity of targeted features made by conventional lithographic techniques, such as UV lithography (450 nm to 10 nm), immersion lithography, EUV or e-beam. The invention relates to novel compositions comprising at least one novel random copolymer which is both cross-linkable and graft-able. More than one such novel copolymer may be used in the present novel composition. The novel composition comprises only random copolymer(s). The novel copolymer, when coated from a novel composition comprised of the novel copolymer and a solvent has a neutral interaction with respect to the alignment of the block copolymer used for self-assembly and directed self-assembly processes, but is also as the novel copolymer capable of both a high degree of crosslinking and also grafting to the substrate such that the neutral layer remains neutral and is not deleteriously affected by the processes that occur over the neutral layer, such as intermixing with the layers coated over the neutral layer, developing, irradiation, stripping, etc. The novel copolymer unexpectedly provides a novel composition which forms a layer upon coating on a substrate with an optimal level of both neutrality to the block copolymers and also crosslinking and grafting to the substrate which prevent undesirable damage to the neutral layer due to subsequent processing while at the same time preventing branching delamination defect caused by delamination of the neutral layer from the substrate.

We had previously shown in U.S. Pat. No. 8,691,925, incorporated herein by reference, that the presence of a high amount of crosslinking benzocyclobutene moiety in copolymers used in a neutral layer application eliminated the solvent treatment step which is needed in many other neutral layer materials without this feature. Such solvent treatment is normally required to remove partially cross-linked surface material even after high post applied bake temperatures (such as 200° C.). This was contrary to the belief that introducing higher than about 2 mole % of the crosslinking unit (3) would destroy neutrality toward the self-assembly block copolymer. However, while neutral layers containing high amounts of crosslinking benzocyclobutene moieties do maintain neutrality, unexpectedly, some films formed from these copolymer unfortunately tended to undergo, after curing, a delamination process which leads to de-wetting defects.

We have unexpectedly found that the novel copolymers when formulated in a composition comprised of the novel polymer and a solvent and coated on a substrate via a novel process can provide and maintain a cross-linked layer and grafted layer with very good film uniformity across a substrate on which it is coated without any de-wetting defects and also act as a neutral layer towards block copolymers during processing involving self-assembly.

The novel copolymer containing crosslinking benzocyclobutene moieties, the novel copolymer is comprised of a copolymer having at least one unit of structure (1), at least one unit of structure (2) and, at least one unit of structure (3) one ⌇ H end group and one end group containing a benzylic alcohol moiety having structure (1');

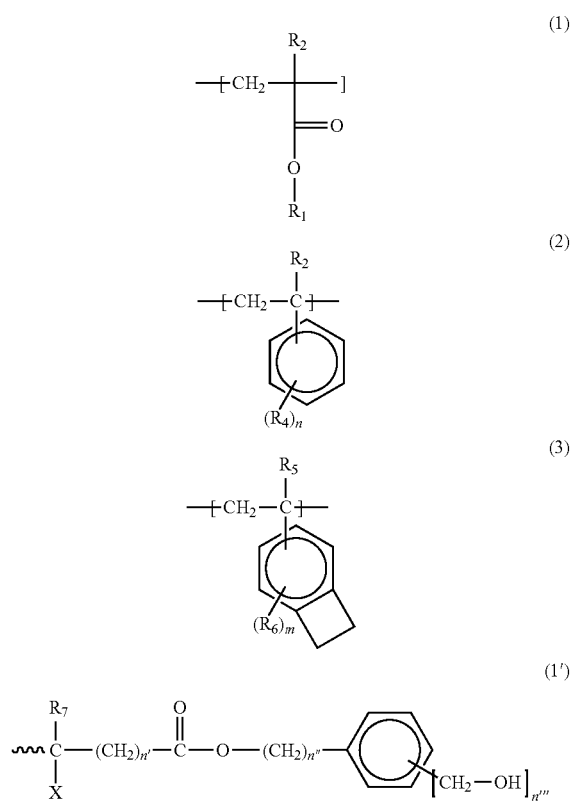

where R$_1$ is selected from the group consisting of a C$_1$-C$_8$ alkyl, C$_1$-C$_8$ fluoroalkyl, C$_1$-C$_8$ partially fluorinated alkyl moiety, C$_4$-C$_8$ cycloalkyl, C$_4$-C$_8$ cyclofluoroalkyl, C$_4$-C$_8$ partially fluorinated cycloalkyl, and a C$_2$-C$_8$ hydroxyalkyl; R$_2$, R$_3$ and R$_5$ are independently selected from a group consisting of H, C$_1$-C$_4$ alkyl, CF$_3$ and F; R$_4$ is selected from the group consisting of H, C$_1$-C$_8$ alkyl, C$_1$-C$_8$ partially fluorinated alkyl moiety and C$_1$-C$_8$ fluoroalkyl, n ranges from 1 to 5, R$_6$ is selected from the group consisting of H, F, C$_1$-C$_8$ alkyl and a C$_1$-C$_8$ fluoroalkyl and m ranges from 1 to 3, and n' ranges from 1 to 5, and n" ranges from 1 to 5, n''' ranges from 1 to 5, R$_7$ is a C$_1$ to C$_8$ alkyl and X is —CN, or an alkyloxycarbonyl moiety R$_8$—O—(C═O)— where R$_8$ is a C$_1$ to C$_8$ alkyl and ⌇ represent the attachment point of the end group to the copolymer. In one embodiment n''' is 1. Novel composition comprised of this novel copolymer and a solvent may contain one or move novel copolymers and a solvent.

The novel composition of this invention is comprised the above described novel copolymer and a solvent.

The novel process of coating the novel composition comprises coating this novel composition on a substrate and first baking the film at a lower temperature to affect solvent removal and grafting of the of the copolymer on the substrate through the benzylic end groups, followed by a higher temperature bake to affect crosslinking of the neutral layer copolymer through the pendant benzocyclobutane groups.

In this novel copolymer the repeat unit having structure (3) the benzocyclobutene moiety provides the copolymer with a site for crosslinking, while the benzylic alcohol containing end group moiety of structure (1') provides a reactive site which allows the novel copolymer, when formulated in the novel composition of this invention comprised of this polymer and a solvent and coated as film on a substrate to be grafted onto this substrate, to form a novel cross-linked and grafted polymer film. Examples of substrates on which this grafted and cross-linked film can be formed are semiconductor (e.g. Si, GaAs, and the like), metal (Cu, W, Mo, Al, Zr, Ti, Hf, Au and the like) and metal oxide (Copper oxide, Aluminum oxide, Hafnium oxide, Zirconium oxide, Titanium oxide and the like). In one embodiment of this invention such grafted crosslinked films act as neutral layers towards self-assembly of the domains of a block copolymer film coated on top of the novel crosslinked and grafted polymer film coated on the substrate.

In one embodiment of this invention these novel copolymers contain a high level of crosslinking benzocyclobutane pendant group, crosslinking unit (3) greater than 2 mole %. In another embodiment of this invention repeat unit (3) is present at greater than 10 mole %.

In one embodiment, the novel copolymer may be represented by structure 4, where X, Y and Z are the mole % of each the repeat units. In one embodiment the sum of X, Y and Z is 100% of the repeat units present and other variables are as previously defined. In one embodiment of this aspect of the invention n''' is one.

In another embodiment the novel copolymer may be represented by structure 4', where X, Y and Z are the mole % of each the repeat units. In one embodiment the sum of X, Y and Z is 100% of the repeat units present and other variables are as previously defined.

In a further embodiment of the novel copolymer may be represented by structure 4'' where X, Y and Z the mole % of each are the repeat units. In one embodiment the sum of X, Y and Z is 100% of the repeat units present and other variables are as previously defined.

In a further embodiment of the novel copolymer may be represented by structure 4''' where X, Y and Z are the mole % of each the repeat units. In one embodiment the sum of X, Y and Z is 100% of the repeat units present and other variables are as previously defined.

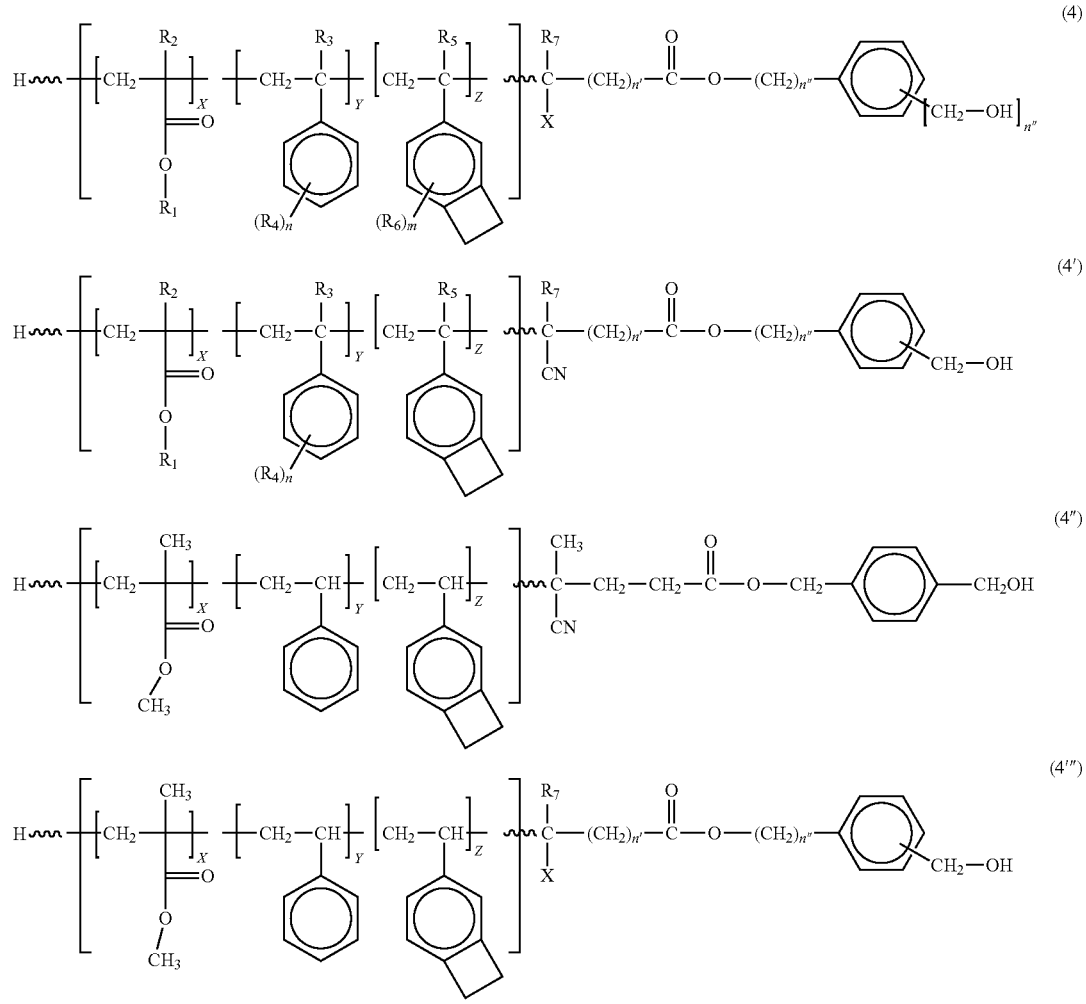

The novel random copolymer can be prepared by using an diazo initiator having structure (5) used to polymerize a mixture of monomers having structures (1"), (2") and (3"); where $R_1$ is selected from the group consisting of a $C_1$-$C_8$ alkyl, $C_1$-$C_8$ fluoroalkyl, $C_1$-$C_8$ partially fluorinated alkyl moiety, $C_4$-$C_8$ cycloalkyl, $C_4$-$C_8$ cyclofluoroalkyl, $C_4$-$C_8$ partially fluorinated cycloalkyl, and a $C_2$-$C_8$ hydroxyalkyl; $R_2$, $R_3$ and $R_5$ are independently selected from a group consisting of H, $C_1$-$C_4$ alkyl, $CF_3$ and F; $R_4$ is selected from the group consisting of H, $C_1$-$C_8$ alkyl, $C_1$-$C_8$ partially fluorinated alkyl moiety and $C_1$-$C_8$ fluoroalkyl, n ranges from 1 to 5, $R_6$ is selected from the group consisting of H, F, $C_1$-$C_8$ alkyl and a $C_1$-$C_8$ fluoroalkyl and m ranges from 1 to 3, and n' ranges from 1 to 5, and n" ranges from 1 to 5, n ranges from 1 to 5, $R_7$ is a $C_1$ to $C_8$ alkyl and X is —CN, or an alkyloxycarbonyl moiety $R_8$—O—(C=O)— where $R_8$ is a $C_1$ to $C_8$ alkyl. In one aspect of this embodiment of the invention n''' is 1.

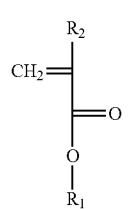

(1")

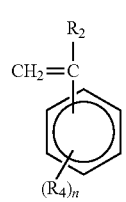

(2")

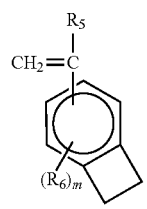

(3")

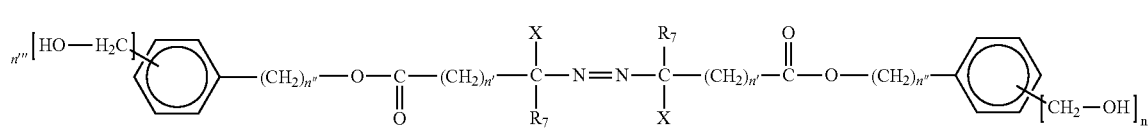

(5)

This initiator produces an end group having structure (6) where the variables are as previously defined. In one aspect of this invention n'''=1.

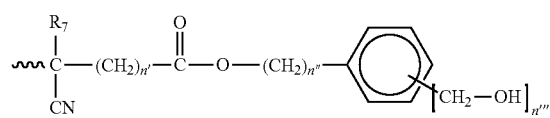

(6)

In another embodiment the diazo initiator has structure (5'),

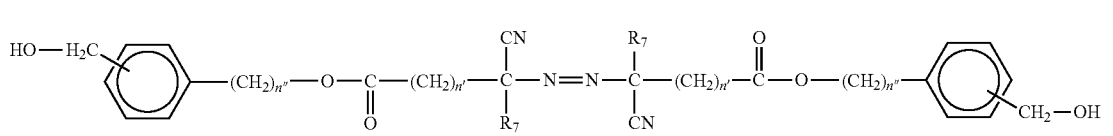

(5')

and produces an end group having structure (6a)

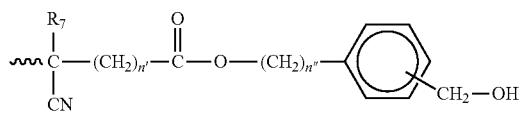

(6a)

In a further embodiment the diazo initiator has structure (5") and produces and end group having structure (7).

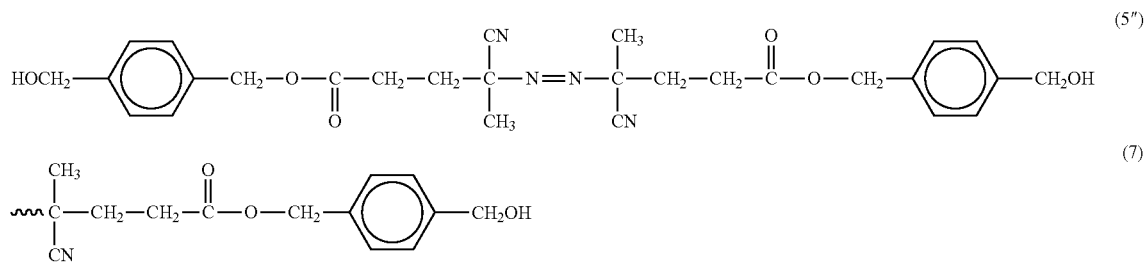

The diazo initiators of structure (5), (5') or (5") provide a hydrogen end group (—H) and an end group having a benzylic alcohol moiety when reacted with a mixture of monomers having structure (1"), (2") and (3"). This polymer structure provides both a benzylic alcohol moiety which can graft onto a substrate and a repeat unit containing a crosslinkable pendant benzocyclobutene moiety. In one embodiment of this inventive copolymer the polymer is synthesized such that the concentration of the unit of structure 3 is greater than 10 mole %; it has been found that having unit (3) greater than 10 mole % does not destroy neutrality toward the block copolymer and has the benefit of dramatically increasing the resistance of the neutral film to undesirable process damage, such as to solvents after post applied bake, which show no detectable film loss in organic solvents, unexpectedly the addition a reactive benzyl alcohol end group having structure (1') that can undergo a grafting reaction on a substrate, prevent de-wetting defect which occur if such a reactive end group is not present.

In this manner, neutrality of the novel neutral layer and good wetting of the neutral layer without formation of defects is sustainable to common lithographic processing steps such as resist coating, resist soft bake, resist exposure, PEB, resist positive-tune and resist negative-tune developments, and resist stripping using organic solvents and TMAH developers.

In a further embodiment, the novel random copolymer comprises units 1, 2 and 3, where unit 1 ranges from about 5 mole % to about 90 mole %; unit 2 ranges from about 5 mole % to about 90 mole % and unit 3 ranges from about 10 mole % to about 60 mole %. In another embodiment the neutral layer comprises units 1, 2 and 3, where unit 1 ranges from about 20 mole % to about 80 mole %; unit 2 ranges from about 20 mole % to about 80 mole % and unit 3 ranges from about 15 mole % to about 45 mole %.

In one embodiment, the novel random copolymer employed herein as neutral layer have a weight-averaged molecular weight ($M_w$) in the range of about 3,000 to about 500,000 g/mol or in another embodiment of about 4,000 to about 200,000, or in another embodiment from about 5,000 to about 150,000. In one embodiment The polydispersity (PD) ($M_w/M_n$) ranges from about 1.5 to about 8, or about 2.0 to about 4, or about 2.0 to about 3.0. Molecular weight, both $M_w$ and $M_n$, can be determined by, for example, gel permeation chromatography using a universal calibration method, calibrated to polystyrene standards.

In one example of an embodiment of a composition comprised of the novel copolymer and a solvent, it may be comprised of a single novel copolymer or as blends of novel copolymers with differing molecular weight, differing concentrations the repeat unit (3) containing a benzocyclobutene pendant group (e.g. 4-vinyl-benzocyclobutene derived repeat unit), differing comonomer ratios, etc. The benzocyclobutene containing monomeric unit (3) can also be employed with varying amounts of monomeric repeat units (1), (2), for example, styrene and methylmethacrylate units, and in addition to these the polymers may be comprise of other repeat units derived from monomers having a single polymerizable vinyl group. The composition of these repeat units can be varied quite substantially while maintaining neutrality towards a block copolymer containing the corresponding repeat units in a large range of blending compositions. This allows one to optimize a neutral layer for instance by adjusting the composition of a binary blend containing two different neutral copolymers containing different ratios of repeat units so as to maximize the effectiveness of a particular self-directed approach such a graphoepitaxy or chemoepitaxy in imparting pattern rectification and/or pattern multiplication for a given array of repeating features such as L/S or CH patterns. A single copolymer may also be used in the novel composition. In one embodiment of the present invention the neutral layer composition comprises a blend of two or more different composition of the novel copolymer. The novel composition may comprise a blend of 2 or more copolymers of differing mole % concentration of the units of structure 1, 2 and 3. As an example, the composition comprises a first and second copolymer of differing mole ratios of the monomeric units; a first copolymer where the unit of structure 1 is from about 5 mole % to about 90 mole %, structure of unit 2 is from about 5 mole % to about 90 mole % and structure 3 is from about 10 mole % to about 60 mole %; a second copolymer where the unit of structure 1 is from about 5 mole % to about 90 mole %, structure of unit 2 is from about 5 mole % to about 90 mole % and structure 3 is from about 10 mole % to about 60 mole %.

The solid components of the novel composition, which may be used as a neutral layer are mixed with a solvent or mixtures of solvents that dissolve the solid components. Suitable solvents may include, for example, a glycol ether derivative such as ethyl cellosolve, methyl cellosolve, propylene glycol monomethyl ether (PGME), diethylene glycol monomethyl ether, diethylene glycol monoethyl ether, dipropylene glycol dimethyl ether, propylene glycol n-propyl ether, or diethylene glycol dimethyl ether; a glycol ether ester derivative such as ethyl cellosolve acetate, methyl cellosolve acetate, or propylene glycol monomethyl ether acetate (PGMEA); carboxylates such as ethyl acetate, n-butyl acetate and amyl acetate; carboxylates of di-basic acids such as diethyloxylate and diethylmalonate; dicarboxylates of glycols such as ethylene glycol diacetate and propylene glycol diacetate; and hydroxy carboxylates such as methyl lactate, ethyl lactate (EL), ethyl glycolate, and ethyl-3-hydroxy propionate; a ketone ester such as methyl pyruvate or ethyl pyruvate; an alkoxycarboxylic acid ester such as methyl 3-methoxypropionate, ethyl 3-ethoxypropionate, ethyl 2-hydroxy-2-methylpropionate, or methylethoxypropionate; a ketone derivative such as methyl ethyl ketone, acetyl acetone, cyclopentanone, cyclohexanone or 2-heptanone; a ketone ether derivative such as diacetone alcohol methyl ether; a ketone alcohol derivative such as acetol or diacetone alcohol; a ketal or acetal like 1,3 dioxalane and diethoxypropane; lactones such as butyrolactone; an amide derivative such as dimethylacetamide or dimethylformamide, anisole, and mixtures thereof.

The novel composition, in addition to the solvent, may contain surfactants as additives to facilitate coating.

Also, the novel composition may optionally comprise an acid generator such as a thermal acid generator and/or a photoacid generator. Although such additives are not required for assisting the crosslinking of the pendant benzocyclobutane group (i.e. in repeat unit 3), these additives by releasing acid may assist in the grafting reaction of the benzyl alcohol end group moiety (i.e. end group 1') on a substrate. This may both assist in accessing a higher level of grafting reaction at the substrate surface and may also allow the bake temperature needed to affect grafting after coating to be lowered.

Suitable thermal acid generators include the onium salts, halogen containing compounds, perfluorobenzene sulfonate esters, perfluoroalkane sulfonate esters. Without limitation, exemplary thermal acid generators for the above formulation include tri-$C_1$-$C_8$-alkylammonium p-toluenesulfonate, $C_1$-$C_8$-alkylammonium dedecylbenzenesulfonate, tri-$C_1$-$C_8$-alkylammonium perfluorobutane-1-sulfonate, tri-$C_1$-$C_8$-alkylammonium trifluoromethane-sulfonate, N-hydroxyphthalimide trifluoromethane-sulfonate, bis(4-t-butyl phenyl)iodonium trifluoromethane sulfonate, bis(4-t-butyl phenyl)iodonium perfluoro-1-butanesulfonate, bis(4-t-butyl phenyl)iodonium perfuoro-I-octanesulfonate, bis(phenyl)iodonium hexafluoroantimonate, N-hydroxy-5-norbornene-2,3-dicarboximide perfluorol-butanesulfonate, 2-nitrobenzyl trifluoromethanesulfonate, 4-nitrobenzyl trifluoromethanesulfonate, 2-nitrobenzyl perfluorobutane sulfonate, 4-nitrobenzyl perfluorobutanesulfonate or a combination comprising at least one of the foregoing. Suitable photoacid generators include, for example, aromatic and aliphatic sulfonium salts and iodonium salts.

One embodiment of this invention is a process for forming a grafted and crosslinked coating of the novel copolymer from the novel composition comprised of this copolymer and a solvent (in any of its different embodiments) on a substrate where the process is comprised of steps a) to c):
  a) forming a coating of the novel copolymer composition on a substrate;
  b) heating the coating at a temperature between 90° C.-180° C. to remove solvent and form a grafted copolymer coating layer;
  c) heating the coating at a temperature between 220° C.-250° C. to form a cross-linked copolymer coating layer.

In another embodiment of this process in the novel composition step b) to remove solvent and graft the copolymer on the substrate, this step maybe done at temperatures ranging from about 90° C.-180° C., or about 150° C.-180° C., or from about 160° C.-175° C., or about 165° C.-170° C. The time for removing solvent and graft the copolymer on the substrate is about 1-10 minutes or about 2-5 minutes. In a further aspect of this embodiment the crosslinking bake c) is done at about 220° C.-300° C., or in another embodiment about 220° C.-250° C. or in still another embodiment about 230° C.-240° C. The heating time to crosslink in the copolymer film in step c) is 1-10 minutes, or in another embodiment 2-5 minutes In another embodiment of this invention, the novel composition is coated on a substrate and heated once to remove the solvent and graft the copolymer on the substrate and heated a second time to crosslink the film. Typical film thickness range from about 3 nm to about 50 nm after heating, or about 3 nm to about 30 nm, or about 4 nm to about 20 nm, or about 5 nm to about 20 nm, or about 10 nm to about 20 nm. To remove solvent and graft the copolymer on the substrate, the film can be heated at temperatures ranging from about 90° C.-180° C., or about 150° C.-180° C., or from about 160° C.-175° C., or about 165° C.-170° C. The heating time for removing solvent and graft the copolymer on the substrate is about 1-10 minutes or in another embodiment about 2-5 minutes.

If a thermal acid generator is present as an additive the temperature needed to affect solvent removal and grafting may be from about 90° C. to about 170° C., or about 100° C. to about 170° C. Here also, the time for removing solvent and graft the copolymer on the substrate is about 1-10 minutes or in another embodiment about 2-5 minutes.

If a photoacid generator is present, the acid is released during an optional blanket irradiation step with UV, deep UV or VUV radiation after a bake to remove solvent only in the range of about 90 to about 150° C. Subsequent to the irradiation step for photoacid generators releasing a high acidity photoacid (i.e. pKa <−2) it may be possible to affect grafting without a subsequent grafting bake step or to proceed with a moderate grafting bake step from about 90 to about 150° C. Otherwise, for photoacid generators releasing a lower acidity photoacid (i.e. pKa ≥−2) a baking temperature in the range of about 90 to about 200° C. may be employed.

Generally, the heating time to remove solvent and graft the copolymer to the substrate is 1-10 minutes, or another embodiment 2-5 minutes.

After the solvent/grafting bake is complete a crosslinking bake is done at about 200° C. to about 300° C., or in another embodiment about 220° C. to about 300° C., or in another embodiment about 220° C. to about 250° C. or in still another embodiment about 230° C. to about 240° C. The heating time to crosslink the copolymer film is 1-10 minutes, or in another embodiment 2-5 minutes Once the cross-linked film has been formed the coating may be used for further processing to finally form a pattern using any self-directed assembly techniques where the cross-linked and grafted layer is used as a neutral layer in self-self-assembly processes. Examples of such techniques are self-assembly on an unpatterned substrate coated with the novel coated, grafted and cross-linked composition; graphoepitaxy where the substrate coated with the novel coated, grafted and cross-linked composition also contains a topographical pattern overlying this layer; and chemoepitaxy, where the substrate coated with the novel coated, grafted and cross-linked composition substrate is also patterned with areas where the surface is free of the neutral layer and has a different chemical composition enabling it to act as a pinning area. The cross-linked and grafted neutral layers formed by the novel copolymer composition remain neutral despite any damage that might occur during the lithographic processes where the cross-linked neutral layer is used, such as dissolution from organic solvents (such as solvents used to form coatings above the neutral layer, solvent developers, etc.), dissolution in aqueous alkaline developers, damage from processes used to image the photoresist coated over the neutral layer (such as e-beam, EUV, deep UV, etc.), or dissolution in photoresist strippers. The cross-linked layers are not soluble in solvents such as those that are used to coat the photoresist, such as PGMEA, PGME, EL, etc.

A specific embodiment of a process of self-assembly of a block copolymer on an unpatterned substrate enabled by the novel composition of this invention is comprised of the following steps where the cross-linked, grafted coating formed by the novel composition acts as a neutral layer:
 a) forming a coating of the novel copolymer composition of this invention on a substrate;
 b) heating the coating at a temperature between 90° C.-180° C. to remove solvent and to form a grafted copolymer coating layer;
 c) heating the coating at a temperature between 200° C.-300° C. to form a cross-linked copolymer forming the neutral coating layer;
 d) applying a block copolymer over the neutral coating layer and annealing until directed self-assembly of the block copolymer layer occurs.

In this embodiment the temperature in step b) and c) may be varied as previously described for the process of forming a grafted cross-linked coating of the novel copolymer of this invention. Also, the baking time of each of these steps may varied as previously described. In another embodiment of this aspect of the invention is to form an image in the substrate by having a step e) following step d) in which the self-assembled bock copolymer domains are used to provide a selective barrier against etching into the substrate. This selectivity may either be imparted by a differing reactivity of the assembled block domains towards a chemical etchant, or by a differing reactivity towards a plasma etching step, used to etch the substrate. One example is when one block is plasma etch resistant block and the other is highly etchable by the plasma. This selective etching into the substrate by the self-assembled block copolymer may be used to provide an image into the substrate.

Specific examples of directed self-assembly processes which may be employed with the novel copolymer composition of this invention capable of forming a coating grafted and cross-linked neutral layer on a patterned substrate are graphoepitaxy and chemoepitaxy.

One embodiment of this is when the graphoepitaxy directed self-assembly process is comprised of the following steps:
 a) forming a coating of the novel copolymer composition of this invention on a substrate;
 b) heating the copolymer coating layer at a temperature between 90° C.-180° C. to remove solvent and form a grafted copolymer coating;
 c) heating the grafted copolymer coating layer at a temperature between 200° C.-300° C. to form a cross-linked neutral layer;
 d) providing a coating of a photoresist layer over the cross-linked grafted neutral layer;
 e) forming a pattern in the photoresist;
 f) applying a coating of a block copolymer solution on the pattern, where the block copolymer comprises an etch resistant and etchable block and annealing until directed self-assembly of the block copolymer occurs.

In this embodiment of graphoepitaxy the temperature in step b) and c) may be varied, as previously described for the process of forming a grafted cross-linked coating of the novel copolymer of this invention. Also, the baking time of each of these steps may be done as previously described. In another embodiment of this aspect of the invention is to form an image into the substrate by having a step g) following step f) in which the self-assembled bock copolymer domains are used to provide a selective barrier against etching into the substrate. This selectivity etching may either be imparted by a differing reactivity of the assembled block domains towards a chemical etchant, or by a differing reactivity towards a plasma etching step, used to etch the substrate. One example is when one block is plasma etch resistant block and the other is highly etchable by the plasma. Selective etching into the substrate by the self-assembled block copolymer may be used to provide an image into the substrate. In turn this image may be used to in the manufacture of microelectronic devices by defining structures in specific layers employed in a process to make a memory or logic device. Negative or positive resists may be employed in step e). Also, the radiation used to form the photoresist pattern formed in step e) may be selected from the consisting of e-beam, broadband, 193 nm immersion lithography, 13.5 nm, 193 nm, 248 nm, 365 nm and 436 nm radiation.

Another embodiment of directed self-assembly is a process of chemoepitaxy, directed self-assembly of a block copolymer layer comprised of the steps:
 a) forming a coating of the copolymer composition of claim 1 on a substrate;
 b) heating the copolymer coating layer at a temperature between 90° C.-180° C. to remove solvent and form a grafted copolymer coating layer;
 c) heating the grafted copolymer coating layer at a temperature between 200° C.-300° C. to form a cross-linked coating, forming the neutral layer;
 d) providing a coating of a photoresist layer over the cross-linked and grafted neutral layer;
 e) forming a pattern in the photoresist layer forming regions in which the cross-linked and grafted neutral layer region is not covered by a photoresist;
 f) treating the uncovered neutral layer,
 g) removing the photoresist,
 h) applying a block copolymer comprising an etch resistant block and highly etchable block over the neutral layer and annealing until directed self-assembly occurs; and, In this embodiment of chemoepitaxy the temperature in step b) and c) may be varied, as previously described for the process of forming a grafted cross-linked coating of the novel copolymer of this invention. Also, the baking time of each of these steps may be done as previously described. In step f) the treatment may be one in which the uncovered is reacted with a liquid etchant or plasma etchant to turn it into a pinning region showing a high degree of selectivity during directed self-assembly towards one of the block of the block copolymer coated in step h). Another embodiment of this aspect of the invention is to form an image into the substrate by having a step i) following step h) in which the self-assembled bock copolymer domains are used to provide a selective barrier against etching into the substrate. This selectivity etching may either be imparted by a differing reactivity of the assembled block domains towards a chemical etchant, or by a differing reactivity towards a plasma etching step, used to etch the substrate. One example is when one block is plasma etch resistant block and the other is highly etchable by the plasma. Selective etching into the substrate by the self-assembled block copolymer may be used to provide an image into the substrate. In turn this image may be used to in the manufacture of microelectronic devices by defining structures in specific layers employed in a process to make a memory or logic device. Negative or positive resists may be employed in step e). Also, the radiation used to form the photoresist pattern formed in step e) may be selected from the consisting of e-beam, broadband, 193 nm immersion lithography, 13.5 nm, 193 nm, 248 nm, 365 nm and 436 nm radiation.

In the self-assembly process, and in directed self-assembly processes such as graphoepitaxy or chemoepitaxy, the block copolymer for use in conjunction with the novel copolymer composition capable of forming a neutral layer can be any block copolymers which can form domains through self-assembly. The microdomains are formed by blocks of the same type which tend to self-associate. Typically, block copolymer employed for this purpose are polymers in which the repeat units derived from monomers are arranged in blocks which are different compositionally, structurally or both and are capable of phase separating and forming domains. The blocks have differing properties which can be used to remove one block while keeping the other block intact on the surface, thus providing a pattern on the surface. Thus, the block may be selectively removed by plasma etching, solvent etching, developer etching using aqueous alkaline solution, etc. In block copolymers based on organic monomers, one block can be made from polyolefinic monomers including polydienes, polyethers including poly(alkylene oxides) such as poly(ethylene oxide), poly(propylene oxide), poly(butylene oxide) or mixtures thereof; and, the other block can be made from different monomers including poly((meth)acrylates), polystyrenes, polyesters, polyorganosiloxanes, polyorganogermanes, and or mixtures thereof. These blocks in a polymer chain can each comprise one or more repeat units derived from monomers. Depending on the type of pattern needed and methods used different types of block copolymers may be used. For instance, these may consist of diblock copolymers, triblock copolymers, terpolymers, or multiblock copolymers. The blocks of these block copolymers may themselves consist of homopolymers or copolymers. Block copolymers of different types may also be employed for self-assembly, such as dendritic block copolymers, hyperbranched block copolymers, graft block copolymers, organic diblock copolymers, organic multiblock copolymers, linear block copolymers, star block copolymers amphiphilic inorganic block copolymers, amphiphilic organic block copolymers or a mixture consisting of at least block copolymers of different types.

The blocks of organic block copolymer may comprise repeat units derived from monomers such as $C_{2-30}$ olefins, (meth)acrylate monomers derived from $C_{1-30}$ alcohols, inorganic-containing monomers including those based on Si, Ge, Ti, Fe, Al. Monomers based on $C_{2-30}$ olefins can make up a block of high etch resistance alone or do so in combination with one other olefinic monomer. Specific example of olefinic monomers of this type are ethylene, propylene, 1-butene, 1,3-butadiene, isoprene, dihydropyran, norbornene, maleic anhydride, styrene, 4-hydroxy styrene, 4-acetoxy styrene, 4-methylstyrene, alpha-methylstyrene or mixtures thereof. Examples of highly etchable units can be derived from (meth)acrylate monomers such as (meth)acrylate, methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, isopentyl (meth)acrylate, neopentyl (meth)acrylate, n-hexyl (meth)acrylate, cyclohexyl (meth)acrylate, isobornyl (meth)acrylate, hydroxyethyl (meth)acrylate or mixtures thereof.

An illustrative example of a block copolymer containing one type of high etch resistant repeat unit would be a polystyrene block containing only repeat units derived from styrene and another type of highly etchable polymethylmethacrylate block containing only repeat units derived from methylmethacrylate. These together would form the block copolymer poly(styrene-b-methylmethacrylate), where b refers to block.

Specific non-limiting examples of block copolymers that are useful for graphoepitaxy, chemoepitaxy or pinned chemoepitaxy as used for directed self-assembly on a patterned neutral layer, are poly(styrene-b-vinyl pyridine), poly(styrene-b-butadiene), poly(styrene-b-isoprene), poly(styrene-b-methyl methacrylate), poly(styrene-b-alkenyl aromatics), poly(isoprene-b-ethylene oxide), poly(styrene-b-(ethylene-propylene)), poly(ethylene oxide-b-caprolactone), poly(butadiene-b-ethylene oxide), poly(styrene-b-t-butyl (meth)acrylate), poly(methyl methacrylate-b-t-butyl methacrylate), poly(ethylene oxide-b-propylene oxide), poly(styrene-b-tetrahydrofuran), poly(styrene-b-isoprene-b-ethylene oxide), poly(styrene-b-dimethylsiloxane), poly(methyl methacrylate-b-dimethylsiloxane), or a combination comprising at least one of the above described block copolymers. All these polymeric materials share in common the presence of at least one block which is rich in repeat units resistant to etching techniques typically employed in manufacturing IC devices and at least one block which etches rapidly under these same conditions. This allows for the directed self-assembled polymer to pattern transfer onto the substrate to affect either pattern rectification or pattern multiplication.

Typically, the block copolymers employed for the directed self-assembly such as in graphoepitaxy, chemoepitaxy or pinned chemoepitaxy have a weight-averaged molecular weight ($M_w$) in the range of about 3,000 to about 500,000 g/mol and a number averaged molecular weight ($M_n$) of about 1,000 to about 60,000 and a polydispersity ($M_w/M_n$) of about 1.01 to about 6, or 1.01 to about 2 or 1.01 to about 1.5. Molecular weight, both $M_w$ and $M_n$, can be determined by, for example, gel permeation chromatography using a universal calibration method, calibrated to polystyrene standards. This ensures that the polymer blocks have enough mobility to undergo self-assembly when applied to a given surface either spontaneously, or by using a purely thermal treatment, or through a thermal process which is assisted by the absorption of solvent vapor into the polymer framework to increase flow of segments enabling self-assembly to occur.

Solvents suitable for dissolving block copolymers for forming a film can vary with the solubility requirements of the block copolymer. Examples of solvents for the block copolymer assembly include propylene glycol monomethyl ether acetate (PGMEA), ethoxyethyl propionate, anisole, ethyl lactate, 2-heptanone, cyclohexanone, amyl acetate, n-butyl acetate, n-amyl ketone (MAK), gamma-butyrolactone (GBL), toluene, and the like. In an embodiment, specifically useful casting solvents include propylene glycol monomethyl ether acetate (PGMEA), gamma-butyrolactone (GBL), or a combination of these solvents.

The block copolymer composition can comprise additional components and/or additives selected from the group consisting of: inorganic-containing polymers; additives including small molecules, inorganic-containing molecules, surfactants, photoacid generators, thermal acid generators, quenchers, hardeners, cross-linkers, chain extenders, and the like; and combinations comprising at least one of the foregoing, wherein one or more of the additional components and/or additives co-assemble with the block copolymer to form the block copolymer assembly.

The block copolymer composition is applied to a pattern of the novel neutral layer which has been defined on a surface by conventional lithography, where the neutral surface is a cross-linked coating formed from the novel composition. Upon application and solvent removal, the block copolymer then undergoes self-assembly directed by the specific pattern formed by conventional lithographic processing over the neutral layer through either actual topographical features or a patterned chemical difference of the substrate surface created by conventional lithographic process. Either pattern rectification maintaining the same resolution is achieved and/or pattern multiplication may also be achieved if multiple phase boundaries are formed between the features defined with conventional lithography, depending on the relative pitch of the pattern versus the microphase separation distance after standard IC processing to pattern transfer.

The application of the block copolymer by spinning techniques (including spin drying) can suffice to form the self-directed block copolymer assembly. Other methods of self-directed domain formation can occur during applying, baking, annealing, or during a combination of one or more of these operations. In this way, an oriented block copolymer assembly is prepared by the above method, having microphase-separated domains that comprise cylindrical microdomains oriented perpendicular to the neutral surface, or that comprise lamellar domains oriented perpendicular to the neutral surface. Generally, the microphase-separated domains are lamellar domains oriented perpendicular to the neutral surface, which provide parallel line/space patterns in the block copolymer assembly. The domains, so oriented, are desirably thermally stable under further processing conditions. Thus, after coating a layer of a block copolymer assembly including a useful diblock copolymer such as, for example, poly(styrene-b-methyl methacrylate), and optionally baking and/or annealing, the domains of the block copolymer will form on and remain perpendicular to the neutral surface, giving highly resistant and highly etchable regions on the surface of the substrate, which can be further pattern transferred in the substrate layers. The directed self-assembled block copolymer pattern is transferred into the underlying substrate using known techniques. In one example wet or plasma etching could be used with optional UV exposure. Wet etching could be with acetic acid. Standard plasma etch process, such as a plasma comprising oxygen may be used; additionally argon, carbon monoxide, carbon dioxide, $CF_4$, $CHF_3$, may be present in the plasma. FIGS. 1a-1c illustrate a process where the neutral layer is modified to define a patterned chemical affinity, FIG. 1a. The block copolymer is then coated over a chemically modified neutral layer and annealed to form domains perpendicular to the substrate surface, FIG. 1b. One of the domains is then removed to form a pattern on the surface of the substrate, FIG. 1c.

In the present invention the initial photoresist pattern used for forming the directed self-assembly pattern can be defined using either negative or positive photoresists, or either positive tone or negative tone development processes, and imageable using any conventional lithographic techniques, such as e-beam, ion beam, x-ray, EUV (13.5 nm), broadband, or UV (450 nm-10 nm) exposure, immersion lithography, etc. In one embodiment the present invention is particularly useful for 193 nm imagewise exposure using either dry lithography or immersion lithography. For 193 nm lithography a commercially available positive 193 nm photoresist can be employed such as the non-limiting example of AZ AX2110P (available from EMD Performance Materials Corp, Somerville, N.J.), photoresist from Shin-Etsu Chemical Corp., JSR Micro from Japan Synthetic Rubber, and other photoresists available from Fujifilm, TOK, etc. These photoresists may be developed after exposure, and post exposure baked using an aqueous alkaline developer comprising tetramethylammonium hydroxide to give a positive tone pattern or developed using an organic solvent such as n-amyl ketone (MAK), n-butyl acetate, anisole, etc. to give a negative tone pattern. Alternatively, also for 193 nm exposure, commercially available negative tone photoresists may be employed. One particular feature of the present invention is that despite the high level of crosslinking of the neutral layer, unexpectedly neutrality of the neutral layer toward the block copolymer is maintained. The high level of crosslinking is required when processing steps occur, such as overcoating with photoresist, baking the photoresist, exposing the photoresist, developing the photoresist pattern with the developers employed as described above for each type of photoresist, stripping conditions, etc.; but the novel neutral film still retains neutrality thus allowing for proper orientation of the block copolymer domains between the topographical lithographic features. The neutrality is required to control the orientation of the block copolymer during the alignment process, such that the domains of the block copolymer will form on and remain perpendicular to the neutral surface, as shown in FIGS. 1a-1c. FIGS. 1a-1c show how the block copolymer orients itself into domains perpendicular to the substrate and one of the domains is removes to give a pattern on the substrate.

The substrate over which the neutral layer is coated is any required by the device. In one example the substrate is a wafer coated with a layer of high carbon content organic layer with a coating of silicon or titanium containing ARC (high etch resistance to oxygen plasma) over it, which allows pattern transfer of the patterned block copolymer into these coatings. Suitable substrates include, without limitation, silicon, silicon substrate coated with a metal surface, copper coated silicon wafer, copper, aluminum, polymeric resins, silicon dioxide, metals, doped silicon dioxide, silicon nitride, silicon carbide, tantalum, polysilicon, ceramics, aluminum/copper mixtures, glass, coated glass; gallium arsenide and other such Group III/V compounds. These substrates may be coated with antireflective coating(s). The substrate may comprise any number of layers made from the materials described above.

For the present invention a variety of processes involving graphoepitaxy or (pinned) chemoepitaxy may be employed to achieve a directed self-assembly of the aforementioned block copolymer using a neutral layer which is resistant to lithographic processes as described above, especially maintaining neutrality after crosslinking, to control the orientation of the block copolymers relative to the substrate; this directed self-assembly block copolymer coating is then used to form a high resolution pattern using plasma or wet etching to remove the highly etchable domains of the block copolymer. This pattern can then be further transferred into the substrate. In this manner, a variety of high resolution features may be pattern transferred into the substrate achieving either pattern rectification, pattern multiplication or both.

As an example, in graphoepitaxy applications, a structure, such as a photoresist pattern imaged using any photoresist, and formed over the novel neutral layer coated on a substrate using standard lithographic techniques. Other neutral layers which are resistant to lithographic processes and maintain neutrality after crosslinking may be used. The pitch of topographical features imaged through standard lithography using a photoresist on top of a neutral layer is larger than the pitch of the block copolymer assembly. These topographical photoresist features are typically hardened by ultraviolet exposure, baking or a combination of both of these to avoid intermixing of the block copolymer with the photoresist. The hardening conditions are determined by the type of photoresist used. As an example hardening can be a bake for 2 minutes at 200° C. with or without a UV exposure. The block copolymer composition is used to form a coating and then treated to form self-directed domains as described previously. Consequently, the domains of the block copolymer assembly (either spontaneously, through solvent treatment or thermally by annealing) are forced by the constraints of the topographical pattern overlying the critical neutral layer to align in such a way to multiply the spatial frequency of the fine topographical photoresist pattern, that is domains of high etch rate and etch resistant regions are formed perpendicular to the substrate surface. This multiplication of special frequency is the number of repeating sets of features along a given direction of the topographical pattern. Thus, the resulting pattern in the block copolymer assembly (the spatial frequency of the patterned block copolymer assembly) can be doubled, tripled, even quadrupled relative to the spatial frequency of the original fine topographical pattern. The segregation of the domains occurs such that a structure comprising repeating sets of domains is formed between the patterned photoresist topography with a spatial frequency for the domains (given by the number of repeating sets of domains in the given direction) of at least twice that of the spatial frequency for the topographical pattern.

In one embodiment, the present invention relates to a process for using a positive tone photoresist pattern for graphoepitaxy. A neutral layer which is resistant to lithographic processes and maintain neutrality after crosslinking may be used. The process comprises forming a coating of the novel neutral layer composition on a substrate surface; baking the neutral layer to form a cross-linked and neutral layer; providing a coating of a positive acting photoresist layer over the neutral layer; forming a positive pattern in the photoresist; optionally, hardening the positive photoresist pattern by hard baking, UV exposure or a combination of the two; applying a block copolymer comprising an etch resistant block and an etch labile block over the residual positive photoresist pattern and annealing the film stack until directed self-assembly governed by the residual photoresist feature and neutral layer occurs, such that the domains form perpendicular to the substrate surface; and, etching the block copolymer so that the etch labile blocks are removed producing a line multiplication of the original residual pattern. The neutral layer is such that no damage occurs to the neutral layer during lithographic processing, as described previously.

In another embodiment, the present invention relates to a process for using a negative tone photoresist pattern for use in graphoepitaxy. A neutral layer which is resistant to lithographic processes and maintain neutrality after crosslinking may be used. The process comprises forming a coating of the novel neutral layer on a substrate; baking the neutral layer to form a cross-linked and neutral layer; providing a coating of a negative acting photoresist layer over the neutral layer; forming a negative tone pattern in the photoresist; optionally, hardening the photoresist pattern by hard baking, UV exposure or a combination of the two; applying a block copolymer comprising an etch resistant block and an etch labile block to the substrate containing the pattern and annealing the film stack until directed self-assembly governed by the residual photoresist feature and the neutral layer occurs, such that the domains form perpendicular to the substrate surface; and, etching the block copolymer so that the etch labile block are removed producing a line multiplication of the original residual pattern. The neutral layer is such that no damage occurs to the neutral layer during lithographic processing, as described previously.

In chemoepitaxy, the substrate surface provides a pinning surface feature in the novel neutral layer which has a particular chemical affinity towards a block of the block copolymer, and it is this affinity and the presence of the neutral layer which orients the alignment of the block copolymer. A neutral layer which is resistant to lithographic processes and maintain neutrality after crosslinking may be used. The pinning feature may be a patterned photoresist feature on the surface of the novel neutral layer or a patterned opening in the novel neutral layer or a patterned neutral layer whose surface has been suitably treated to provide a patterned pinning surface. The pinning feature with the chemical difference can be created by any method, such as lithographic imaging of the photoresist and/or etching of the neutral layer to expose a patterned surface with a chemical difference, or any other combination of lithographic techniques. The pinning feature may also be created by chemical treatment of the patterned surface of the neutral layer, without removing the neutral layer. Typically, a stack is formed on the substrate comprising a neutral layer coated over a substrate, over which is coated a photoresist layer.

In one embodiment of a negative tone (where the unexposed region is removed to form a pattern) line multiplication chemoepitaxy, a coating of the novel neutral layer is formed on a substrate, such as on an antireflective substrate or any other type of substrate; the neutral layer is heated to form a cross-linked neutral layer; a coating of a photoresist layer is formed over the cross-linked neutral layer; and, the photoresist is imaged to form a pattern with an open or developed trench in the unexposed regions over the neutral layer and substrate stack. Typically a negative tone is obtained by using a negative photoresist which opens the unexposed regions or a positive photoresist which after forming a latent image in the photoresist uses an organic solvent to remove the unexposed regions, thus forming a trench with a narrow opening. A neutral layer which is resistant to lithographic processes and maintain neutrality after crosslinking may be used. Once the pattern is formed over the neutral layer, the trench is treated to have a chemical affinity. The chemical affinity can be achieved by any technique such as by removing the neutral layer, by wet etching or a plasma etch, or can be treated to form a surface with a particular chemical affinity to one of the blocks of the block copolymer. Typically an oxygen containing plasma is used to etch the neutral layer, thus forming a patterned neutral layer over the substrate. The photoresist is then removed. The photoresist may be removed with a wet stripper, such as an organic solvent stripper used for that particular photoresist or by an aqueous alkaline developer. The openings in the neutral layer have a chemical affinity to only one of the blocks in the block copolymer. As an example if the substrate surface is a silicon antireflective coating or an oxide, it will have an affinity towards the acrylate block and not to the styrene block of the block copolymer, thus forming a patterned pinning surface. One particular feature of the present invention is that despite the high level of crosslinking of the neutral layer, unexpectedly; neutrality of the neutral layer is maintained. The high level of crosslinking is required when overcoating with photoresist or developing the photoresist pattern with the developers employed, or stripping the photoresist, as described above for each type of photoresist; thus allowing for proper orientation of the block copolymer domains between the pinning areas created by the above described process. The block copolymer composition is then applied over the patterned neutral layer to form a layer and treated (such as heating to anneal) to form a self-aligned block copolymer with domains of an etch resistant block and an etch labile block perpendicular to the substrate containing the pattern of neutral layer and removed or treated neutral layer; and, further etching the block copolymer so that the etch labile blocks are removed producing a line multiplication of the original lithographic pattern. Removal of one of the blocks may be by plasma or wet etching. Consequently, the resulting pattern in the block copolymer assembly (i.e., the spatial frequency of the patterned block copolymer assembly) can be doubled, tripled, even quadrupled relative to the spatial frequency of the original fine chemical pattern. The domains, so oriented in this manner, should be thermally stable under the processing conditions. For instance when a layer of a block copolymer assembly including a useful diblock copolymer such as, for example, poly(styrene-b-methylmethacrylate), is coated on a chemically patterned neutral layer, the methylmethacrylate block segments will preferentially interact with the areas of the neutral layer which have been etched or treated; this creates pinning sites which constrain the domains of the block copolymer between the pinning sites, and the novel neutral layer forces the block segments of the block copolymer to remain perpendicular to the neutral surface and are constrained by the chemical pattern in the neutral layer. The domains form by lateral segregation of the blocks on the neutral layer between the constraining chemical patterns in the neutral layer. The segregation of the domains occurs such that a structure comprising repeating sets of domains is formed over the chemically patterned neutral layer with a spatial frequency for the domains (given by the number of repeating sets of domains in the given direction) of at least twice that of the spatial frequency for the original chemical pattern in the neutral layer. Finally, as before the directed self-assembled block copolymer pattern in transferred into the underlying substrate using standard plasma or wet etch processes.

In one embodiment of a positive tone line multiplication chemoepitaxy, a conventional positive photoresist may be used to create chemical pinning. This is accomplished by coating a positive photoresist as described previously on the neutral layer of the present invention coated over a substrate and imaging the photoresist such that the image is overexposed, thus reducing the dimensions of the photoresist pattern to create very shallow residual photoresist features, such as residual lines on which the block copolymer may be applied. This very shallow feature has very little topography, about the order of 10 nm to 100 nm width and 5 nm to 30 nm height. These residual features act as a pinning area over the neutral layer when the block copolymer is applied to the surface of the neutral layer with these residual features remaining. As described above, the block copolymer form directed self-aligned domains using the residual features as pinning areas and neutral layer forces the alignment to give domains perpendicular to the substrate. Finally, as before the directed self-assembled block copolymer pattern in transferred into the underlying substrate using standard plasma or wet etch processes.

Figure 2:
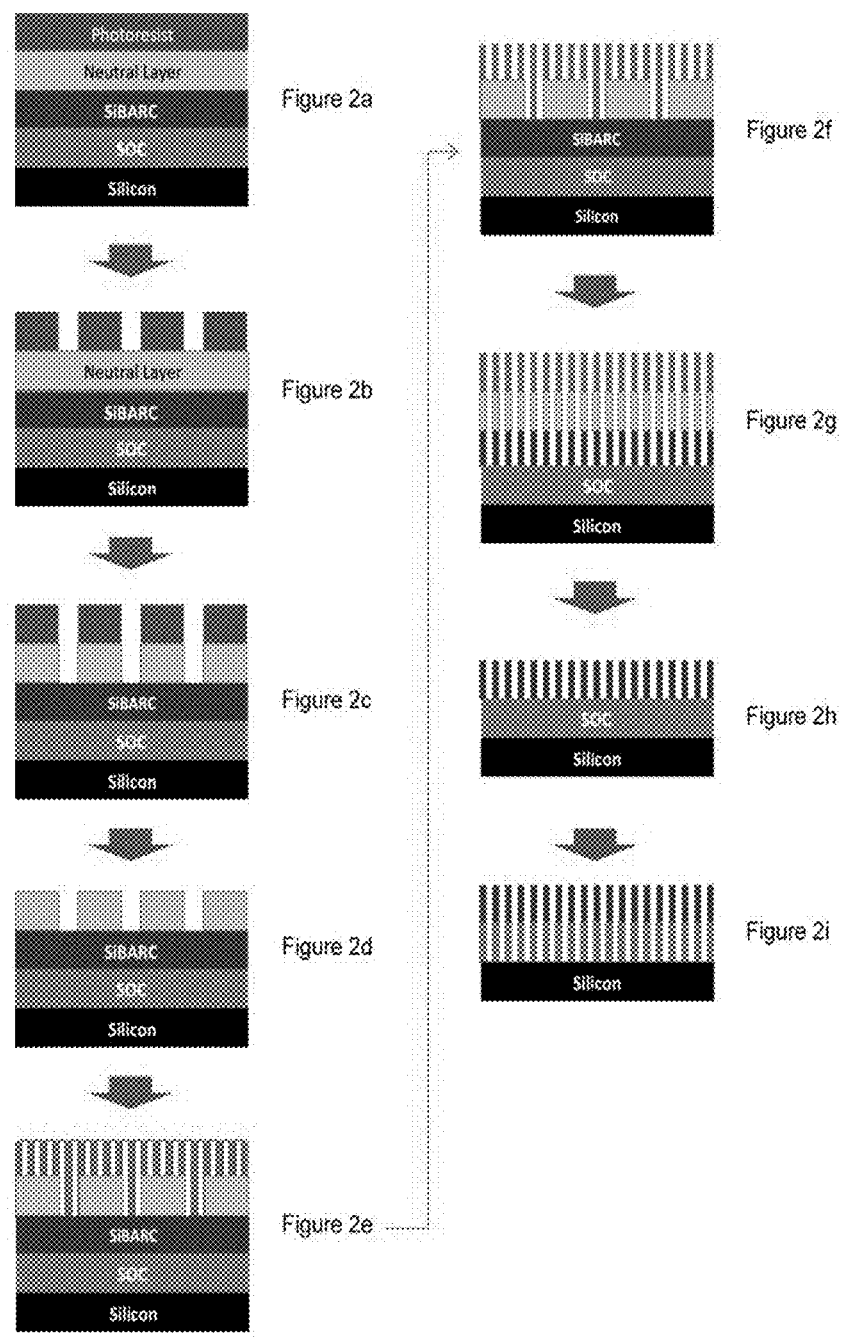
FIGS. 2a to 2i show a process for negative tone line multiplication.

In detail, FIGS. 2 to 4 describe novel processes that use the novel neutral underlayer to obtain high resolution features of the order of nanometers using directed self-assembly of block copolymers.

In the present processes, any type of substrate may be used. As an example, a substrate which has a coating of high carbon underlayer and a silicon antireflective coating may be used as a substrate. The high carbon underlayer can have a coating thickness of about 20 nm to about 2 microns. Over this is coated a silicon antireflective coating of about 10 nm to about 100 nm. The novel neutral layer composition is used to form a coating over the silicon antireflective coating. The neutral layer is coated and baked to form a cross-linked layer of thickness of about 3 nm to about 30 nm, or about 4 nm to about 20 nm, or about 5 nm to about 20 nm, or about 10 nm to about 20 nm. Over the cross-linked neutral layer is coated a photoresist which is formed and imaged using conventional techniques, such as spin coating, baking, and forming an image. FIGS. 2a to 2i illustrate a negative tone line multiplication process. FIGS. 3a to 3g illustrate a positive tone line multiplication process. FIG. 4a 4d illustrate process for contact hole multiplication.

FIGS. 2a to 2i illustrate a novel process for forming line multiplication using a negative tone process. A multilayer stack is formed on a substrate in FIG. 2a, where the stack comprises a substrate comprising a high carbon underlayer and silicon antireflective coating layer, the novel cross-linked neutral layer and a photoresist layer. Any substrate may be used. Any neutral layer which is resistant to lithographic processes and maintains neutrality after crosslinking may be used. The photoresist may be any that is available such as 193 nm photoresist, immersion 193 nm photoresist, e beam photoresist, EUV photoresist, 248 nm photoresist, broadband, 365 nm, 436 nm, etc. The photoresist layer is imaged to form a pattern using conventional techniques. A negative tone photoresist may be used or a positive tone photoresist that uses an organic solvent to develop away the unexposed regions to form very narrow trenches may be used, as shown in FIG. 2b. The novel underlayer is treated to form a pinning surface with a specific chemical affinity to one of the blocks of the block copolymer, using techniques such as plasma etching to remove the layer, plasma etching to modify the surface of the layer, or chemically treating the layer by further deposition of a material or any other pinning methods. A plasma comprising oxygen may be used to remove the neutral layer, as shown in FIG. 2c. The photoresist is then stripped away using solvent stripper or plasma etching, as shown in FIG. 2d. Solvents such as any organic solvents known for removing photoresists may be used, such as PGMEA, PGME, ethyl lactate, etc. The photoresist may also be removed by developing the photoresist pattern in aqueous alkaline developer as commonly used in removing exposed photoresists. The neutral layer on the substrate still maintains its neutrality after the photoresist process steps. Over the patterned neutral layer, FIG. 2e, the composition comprising the block copolymer is coated and treated (such as annealing) to form a self-directed alignment pattern of alternating segments of the block copolymer. A layer which is neutral is required to cause the alignment of the block copolymer to give regions of high etch resistance and regions of low etch resistance, such that pattern multiplication can be achieved, as shown in FIG. 2e; if the neutral layer was not sufficiently neutral then an undesirable orientation parallel to the surface would be achieved. A subsequent etch then removes the highly etchable blocks of the block copolymer, leaving a patterned surface with very high resolution, as shown in FIG. 2f. Typical etch to remove one of the blocks would be a wet or plasma etch as described previously. The pattern may then be transferred in the lower stack layers by plasma etching, as shown in FIGS. 2g to 2i, using etchants for the antireflective coating stack. Typical etch would be a plasma etch dependent on the substrate.

FIGS. 3a to 3g illustrate a novel process for forming line multiplication using a positive tone process. A multilayer stack is formed on a substrate the novel neutral layer and a photoresist layer in FIG. 3a, where the substrate comprises a high carbon underlayer and a silicon antireflective coating layer. Any neutral layer which is resistant to lithographic processes and maintains neutrality after crosslinking may be used. The photoresist may any that are available such as 193 nm photoresist, immersion 193 nm photoresist, e beam photoresist, EUV photoresist, 248 nm photoresist, etc. The photoresist layer is imaged to form a pattern using conventional techniques. A positive tone photoresist is used to form fine photoresist lines, as shown in FIG. 3b. In some cases the photoresist is overexposed, that is given a high energy dose, to form very fine pattern. The very fine photoresist pattern over the novel neutral underlayer is used to form a self-aligned pattern using the block copolymer. The composition comprising the block copolymer is coated and treated (such as annealing) to form a self-directed alignment pattern of alternating segments of the block copolymer. A layer which is neutral is required to cause the alignment of the block copolymer to give regions of high etch resistance and regions of low etch resistance, such that pattern multiplication can be achieved, as shown in FIG. 3c; if the neutral layer was not sufficiently neutral then an undesirable orientation perpendicular to one shown would be achieved. A subsequent etch then removes the highly etchable blocks of the block copolymer, leaving a patterned surface with very high resolution, as shown in FIG. 3d. Typical etch would be a wet or plasma etch as described previously. The pattern may then be transferred in the lower stack layers by plasma etching, as shown in FIG. 3e-g. Typical etch would be plasma etch dependent on the substrate.

FIGS. 4a to 4d illustrate a novel process for forming contact-hole multiplication using a chemoepitaxy process. A multilayer stack is formed on a substrate, where the stack comprises a substrate (such as silicon antireflective coating layer, a titanium antireflective coating, silicon oxide, etc.,), the novel neutral layer and a photoresist layer. A neutral layer which is resistant to lithographic processes and maintain neutrality after crosslinking may be used. The photoresist may be any that are available such as 193 nm photoresist, immersion 193 nm photoresist, e beam photoresist, EUV photoresist, 248 nm photoresist, etc. The photoresist layer is imaged to form a pattern using conventional techniques, FIG. 4a. The novel underlayer is treated to form a pinning surface using techniques such as plasma etching to remove the layer, plasma etching to modify the surface of the layer, or chemically treating the layer by further deposition of a material or any other pinning methods. A plasma comprising oxygen may be used to remove the neutral layer, as shown in FIG. 4b. The photoresist is then stripped away using solvent stripper or plasma etching. Solvents such as any organic solvents known for removing photoresists may be used, such as PGMEA, PGME, ethyl lactate, etc. may be used. The photoresist may also be used by developing the pattern in aqueous alkaline developer used in removing exposed photoresists. The neutral layer on the substrate still maintains its neutrality after the photoresist processing steps. Over the patterned neutral layer, FIG. 4c, the composition comprising the block copolymer is coated and treated (such as annealing) to form a self-directed alignment contact hole pattern of alternating segments of the block copolymer. A layer which remains neutral is required to cause the desired orientation of the block copolymer to give regions of high etch resistance and regions of low etch resistance, such that pattern multiplication can be achieved; if the neutral layer was not sufficiently neutral then an undesirable orientation perpendicular to one shown would be achieved. A subsequent etch then removes the highly etchable blocks of the block copolymer, leaving a patterned surface with very high resolution, as shown in FIG. 4d. Typical etch would be a wet or plasma etch as described previously. The pattern may then be transferred in the lower stack layers by plasma etching. Typical etch would be plasma etch dependent on the substrate. This process can be used for both pattern rectification and pattern pitch frequency multiplication.

The above processes describe novel processes that can be practiced. The process can use the novel neutral layer composition of the present invention.

Each of the documents referred to above are incorporated herein by reference in its entirety, for all purposes. The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

The molecular weight of the copolymers was measured with a Gel Permeation Chromatograph. Chemicals, unless otherwise indicated, were obtained from the Sigma-Aldrich Corporation (St. Louis, Mo.).

Synthesis Example 1

Copolymer of Methyl Styrene, Methyl Methacrylate, and 4-Vinylbenzycylobutene without Graft-Able Benzylic Alcohol End Group Synthesized with AIBN A 1000-ml flask equipped with a condenser, temperature controller, heating mantle and mechanical stirrer were set up. 80.0 grams (0.46 moles) of styrene, 30.8 grams (0.31 moles) of methyl methacrylate, 60 grams (0.46 moles) of 4-Vinylbenzocyclobutene, 2.56 grams of Azobisisobutyronitrile (AIBN) initiator and 400 grams of 2-butanone were added to the flask. The mechanical stirrer was turned on and set up at about 120 rpm. The reaction solution was then degassed by vigorously bubbling nitrogen through the solution for about 30 minutes at room temperature. After 30 minutes of degassing the heating mantle was turned on and the temperature controller was set at 80 C, and the stirred reaction mixture was maintained at this temperature for 20 hours. After this time the heating mantle was turned off and the reaction solution was allowed to cool down to about 40° C. Then the reaction mixture was poured into 12 L of methanol stirred with a mechanical stirring during the addition. During this addition, the polymer was precipitated out. The precipitated polymer was collected by filtration. The collected polymer was dried in vacuum oven at 40° C. About 100 grams of the polymer was obtained. This dried polymer was dissolved in 400 grams of THF and then filtered through a 0.2 um nylon filter. The filtered solution was then precipitated again into a stirred solution of 12 L methanol, the precipitated polymer collected and dried as before under vacuum at 40° C. In this manner, 89 grams (52% yields) of the polymer was obtained after dry. The polymer had an Mw of about 28 k and a polydispersity (PD) of 1.8.

Synthesis Example 2a

Synthesis of Initiator of Structure (5″)

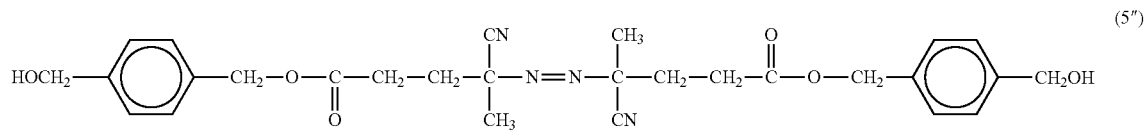

(1) A solution was prepared by dissolving with stirring 5.0 g of 4,4'-azobis(4-cyanovaleric acid) in about 100 mL of methanol. To this was added slowly with stirring a solution consisting of an equimolar amount of tetramethylammonium hydroxide pentahydrate in methanol; stirring was continued for 30 min after the addition was complete. The solution was then concentrated at room temperature with a rotary-evaporator, and the residue poured into diethyl ether which upon stirring yielded viscous oil. The oil was turned into a white solid by stirring it in a mixture of diethyl ether and acetone. Drying at room temperature yielded 5.5 g of the ammonium salt of 4,4'-azobis(4-cyanovaleric acid).

(2) A solution was prepared by dissolving 4 g of 4-(chloromethyl)benzyl alcohol in 30 ml of acetone. To this solution was added 5.7 g of sodium iodide dissolved in 25 g acetone. The mixture was stirred at room temperature for 17 hrs. The formed sodium chloride was filtered out. The filtrate was then concentrated to low volume using a rotary evaporator and poured into stirred DI water. The white solid obtained was isolated, washed thoroughly with deionized (DI) water and dried in a vacuum oven. Yield: 5 g of 4-(iodomethyl)benzyl alcohol.

(3) A solution was prepared by dissolving 4.9 g of 4-(iodomethyl)benzyl alcohol obtained in step (2) in 11 g dimethyl sulfoxide (DMSO). To this solution was added 4.3 g of the ammonium salt prepared in step (1) dissolved in 100 g of DMSO. The reaction mixture was stirred at room temperature for 18 hours. Tetramethylammonium iodide was filtered off to yield a filtrate. The filtrate was poured into DI water under stirring. The formed solid was filtered, washed thoroughly with water, and dried at room temperature giving 4 g of azo initiator with 2 benzyl alcohol groups, (E)-bis(4-hydroxyphenyl) 4,4'-(diazene-1,2-diyl)bis(4-cyanopentanoate). H-1 NMR (CDCl$_3$): 7.32 ppm (doublet, 8H, aromatic CH); 5.09 ppm (singlet, 4H, benzyl ester CH$_2$—O—); 4.65 ppm (doublet, 4H, benzyl alcohol CH$_2$—OH); 2.38 ppm (multiplet, 8H, CH$_2$), 2.1 (broad, 2H, OH), 1.65 (doublet, 6H, CH$_3$).

Synthesis Example 2b

Copolymer of Methyl Styrene, Methyl Methacrylate, and 4-Vinylbenzycylobutene Synthesized with Made with Initiator of Structure (5″) Having Graft-Able Benzylic Alcohol End Group of Structure (7)

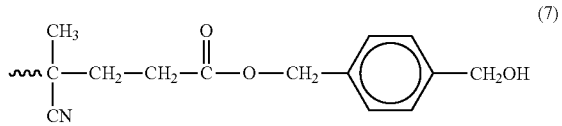

A 500-ml flask equipped with a condenser, temperature controller, heating mantle and mechanical stirrer was set up. To this flask was added 46.8 grams (0.45 moles) of styrene, 60.2 grams (0.60 moles) of methyl methacrylate, 58.6 grams (0.45 moles) of 4-Vinylbenzocyclobutene, 1.32 grams of Diazo-initiator of structure (5″) made in Synthesis Example 2a and 200 grams of 2-butanone. The mechanical stirrer was then turned on and set up at about 120 rpm. The reaction solution was then degassed by vigorously bubbling nitrogen through the solution for about 30 minutes at room temperature. After this time, the heating mantle was turned on and the temperature controller set at 80° C. and the stirred reaction mixture was maintained at this temperature for 20 hours. After this time the heating mantle was turned off and allowed the reaction solution temperature was allowed to cool down to about 40° C. The cooled reaction mixture was then poured into 5 L of methanol which was stirred during the addition with a mechanical stirring.

During this addition the polymer precipitated out. The precipitated solid polymer was collected by filtration. The polymer was then dried in vacuum oven at 40° C. About 80 grams of the polymer was obtained in this manner. The dried polymer was dissolved in 300 grams of THF and then filtered through a 0.2 um nylon filter. The filtered polymer was then precipitated into a stirred solution of methanol as before, collected by filtration and dried under vacuum at 40° C. In this manner, about 76 grams (45% yields) of the polymer was obtained. The polymer had a Mw of about 100 k and a PD=2.5.

Formulation Example 1

A solution was made in PGME comprised of Example 1 (0.3 wt % in PGMEA) which was filtered through a Nylon 0.01 um filter.

Formulation Example 2

A solution was made in PGME comprised of Example 2b (0.3 wt % in PGMEA) which was filtered through a Nylon 0.01 um filter.

Testing Example 1

Inspection of Coating Defect on Film Spun from Synthesis Example 1

A Si-Arc (SHB-9480, Shin-Etsu Chemical Co., Ltd.) was spin-coated at 1500 rpm on a 12 inch silicon wafer and baked at 220° C. for 2 min. Formulation Example 1 was coated on top of the Si-ARC film and baked at 250° C. for 2 min for film x-linking. Then coating was inspected with a defect tool (KLA-2360). Defect images were taken at SEM (SEMvision cX) as shown in FIG. 5 where large tree shape areas of material de-wetting coating defects on substrate were observed.

Testing Example 2

Inspection of Coating Defect on Film Spun from Synthesis Example 2b

A Si-Arc (SHB-9480, Shin-Etsu Chemical Co., Ltd.) was spin-coated at 1500 rpm on a 12 inch silicon wafer and baked at 220° C. for 2 min. Formulation Example 2 was coated on the substrate and baked at 170° C. for 2 min to first graft end functional group on the substrate and then baked again at 240° C. for 2 min for film x-linking. Film was then inspected with defect inspection tool (KLA-2360). No de-wetting defect could be observed.

Testing Example 3

Self Assembly of Block Copolymer on Film of Film of Synthesis Example 2b

A Si-Arc (SHB-9480, Shin-Etsu Chemical Co., Ltd.) was spin-coated at 1500 rpm on a 12 inch silicon wafer and baked at 220° C. for 2 min. Formulation Example 2 was coated on the substrate and baked at 170° C. for 2 min to first graft end functional group on the substrate and then baked again at 240° C. for 2 min for film x-linking. On top of this coating, the block copolymer solution, AZEMBLY™ EXP PME-120 was coated at 1500 rpm and baked at 250° C. for 2 min. Images showing self-assembly of the block copolymer were taken on a NanoSEM (NanoSEM 3D, Applied Materials, Inc.) and a representative image is shown in FIG. 6.

The invention claimed is:

1. A composition comprising at least one random copolymer having at least one unit of structure (1), at least one unit of structure (2), at least one unit of structure (3), one ⌇ H end group, and one end group having structure (1');

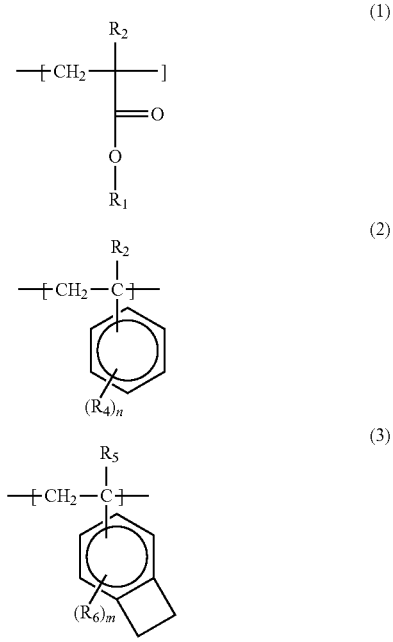

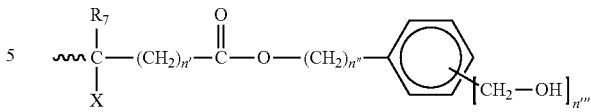

where $R_1$ is selected from the group consisting of a $C_1$-$C_8$ alkyl, $C_1$-$C_8$ fluoroalkyl, $C_1$-$C_8$ partially fluorinated alkyl moiety, $C_4$-$C_8$ cycloalkyl, $C_4$-$C_8$ cyclofluoroalkyl, $C_4$-$C_8$ partially fluorinated cycloalkyl, and a $C_2$-$C_8$ hydroxyalkyl;

$R_2$, $R_3$ and $R_5$ are independently selected from a group consisting of H, $C_1$-$C_4$ alkyl, $CF_3$ and F; $R_4$ is selected from the group consisting of H, $C_1$-$C_8$ alkyl, $C_1$-$C_8$ partially fluorinated alkyl moiety and $C_1$-$C_8$ fluoroalkyl; n ranges from 1 to 5;

$R_6$ is selected from the group consisting of H, F, $C_1$-$C_8$ alkyl and a $C_1$-$C_8$ fluoroalkyl; m ranges from 1 to 3; n' ranges from 1 to 5; n'' ranges from 1 to 5; n''' ranges from 1 to 5; $R_7$ is a $C_1$-$C_8$ alkyl; X is —CN or an alkyloxycarbonyl moiety $R_8$—O—(C=O)— where $R_8$ is a $C_1$-$C_8$ alkyl; and ⌇ represents the attachment point of the end group to the random copolymer, where the composition further comprises a solvent.

2. The composition of claim 1, where the copolymer is capable of forming a layer which is grafted, cross-linked, and a neutral layer relative to a block copolymer.

3. The composition of claim 1, where the copolymer is capable of forming a layer which is a grafted, cross-linked, and a neutral layer which is not soluble in an organic solvent for photoresist.

4. The composition of claim 1, where the copolymer is capable of forming a layer which is a grafted, cross-linked, and a neutral layer which is not soluble in an aqueous alkaline developer.

5. The composition of claim 1, where $R_1$ is selected from the group consisting of a $C_1$-$C_8$ alkyl; $R_2$, $R_3$ and $R_5$ are independently selected from the group consisting of H and $C_1$-$C_4$ alkyl; $R_4$ is selected from the group consisting of H, $C_1$-$C_8$ alkyl, and n=1; and $R_6$ is selected from the group consisting of H, $C_1$-$C_8$ alkyl, and m=1.

6. The composition of claim 1, where the unit of structure (3) ranges from 10 mole % to 45 mole %.

7. The composition of claim 2, where the block copolymer is poly(styrene-b-methylmethacrylate).

8. The composition of claim 1, which further comprises an acid generator.

9. The composition of claim 1, which further comprises a thermal acid generator.

10. A random copolymer having at least one repeat unit of structure (1), at least one repeat unit of structure (2), at least one repeat unit of structure (3) one ⌇ H end group, and one end group having structure (1');

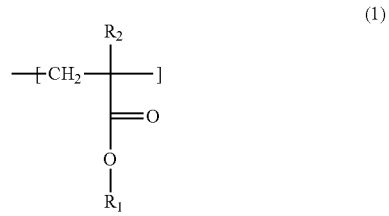

-continued

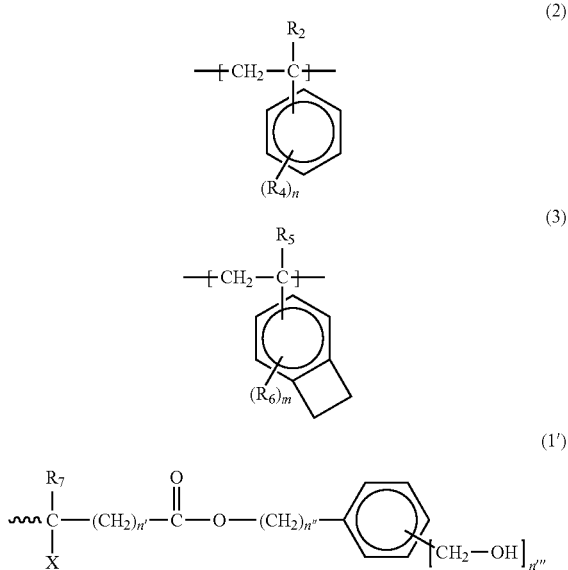

where $R_1$ is selected from the group consisting of a $C_1$-$C_8$ alkyl, $C_1$-$C_8$ fluoroalkyl, $C_1$-$C_8$ partially fluorinated alkyl moiety, $C_4$-$C_8$ cycloalkyl, $C_4$-$C_8$ cyclofluoroalkyl, $C_4$-$C_8$ partially fluorinated cycloalkyl, and a $C_2$-$C_8$ hydroxyalkyl;
$R_2$, $R_3$ and $R_5$ are independently selected from a group consisting of H, $C_1$-$C_4$ alkyl, $CF_3$ and F; $R_4$ is selected from the group consisting of H, $C_1$-$C_8$ alkyl, $C_1$-$C_8$ partially fluorinated alkyl moiety and $C_1$-$C_8$ fluoroalkyl, n ranges from 1 to 5, $R_6$ is selected from the group consisting of H, F, $C_1$-$C_8$ alkyl and a $C_1$-$C_8$ fluoroalkyl and m ranges from 1 to 3, and n' ranges from 1 to 5, and n" ranges from 1 to 5, n'" ranges from 1 to 5, $R_7$ is a $C_1$ to $C_8$ alkyl and X is —CN, or an alkyloxycarbonyl moiety $R_8$—O—(C=O)— where $R_8$ is a $C_1$ to $C_8$ alkyl and ∿∿ represents the attachment point of the end group to the random copolymer where the composition the composition further comprises a solvent.

11. A process for forming a grafted and cross-linked coating of a copolymer on a substrate comprised of the steps:
    a) forming a coating of a composition of claim 1 on a substrate;
    b) heating the coating at a temperature between 90° C.-180° C. to remove solvent and to form a grafted coating layer of the copolymer;
    c) heating the grafted coating layer at a temperature between 200° C.-250° C. to form a cross-linked copolymer coating layer.

12. A process for forming a self-assembled block copolymer coating layer on a neutral layer coating comprised of the steps:
    a) forming a coating of a composition of claim 1 on a substrate;
    b) heating the coating at a temperature between 90° C.-180° C. to remove solvent and to form a grafted coating layer of the copolymer;
    c) heating the grafted coating layer at a temperature between 200° C.-250° C. to cross-link the copolymer forming the neutral coating layer;
    d) applying a block copolymer over the neutral coating layer and annealing until directed self-assembly of the block copolymer layer occurs.

13. A process of graphoepitaxy, directed self-assembly of a block copolymer layer used to form an image comprised of the steps:
    a) forming a coating of a composition of claim 1 on a substrate;
    b) heating the coating at a temperature between 90° C.-180° C. to form a grafted coating layer;
    c) heating the grafted coating layer at a temperature between 200° C.-300° C. to form a cross-linked, grafted neutral layer;
    d) providing a coating of a photoresist layer over the cross-linked, grafted neutral layer;
    e) forming a pattern in the photoresist layer via exposure and development;
    f) applying a block copolymer comprising an etch resistant block and a highly etchable block over the photoresist pattern and annealing until directed self-assembly occurs; and,
    g) etching the block copolymer, thereby removing the highly etchable block of the copolymer and forming a pattern.

14. The process of claim 13 where the pattern in the photoresist layer is formed by imaging lithography selected from a group consisting of e-beam, broadband, 193 nm immersion lithography, 13.5 nm, 193 nm, 248 nm, 365 nm and 436 nm.

15. A process of chemoepitaxy, directed self-assembly of a block copolymer layer used to form an image comprised of the steps:
    a) forming a coating of a composition of claim 1 on a substrate;
    b) heating the coating at a temperature between 90° C.-180° C. to remove solvent and form a grafted coating layer;
    c) heating the grafted coating layer at a temperature between 200° C.-300° C. to form a cross-linked, grafted neutral layer;
    d) providing a coating of a photoresist layer over the cross-linked, grafted neutral layer;
    e) forming a pattern in the photoresist layer, via exposure and development thereby forming regions in which the neutral layer is uncovered by the resist;
    f) treating the uncovered neutral layer,
    g) removing the photoresist,
    h) applying a block copolymer comprising an etch resistant block and a highly etchable block over the neutral layer and annealing until directed self-assembly occurs; and,
    i) etching the block copolymer, thereby removing the highly etchable block of the copolymer and forming a pattern.

16. The process of claim 14 where the pattern in the photoresist layer is formed by imaging lithography selected from a group consisting of e-beam, broadband, 193 nm immersion lithography, broadband, 13.5 nm, 193 nm, 248 nm, 365 nm and 436 nm.

* * * * *